(12) United States Patent
Webster et al.

(10) Patent No.: US 11,065,463 B2
(45) Date of Patent: Jul. 20, 2021

(54) WEARABLE CARDIOVERTER DEFIBRILLATOR (WCD) SYSTEM HAVING WCD MODE AND ALSO AED MODE

(71) Applicant: West Affum Holdings Corp., Grand Cayman (KY)

(72) Inventors: Brian D. Webster, Sammamish, WA (US); Zoie Engman, Kirkland, WA (US); Phillip D. Foshee, Jr., Woodinville, WA (US); David P. Finch, Bothell, WA (US); Joseph L. Sullivan, Kirkland, WA (US); Gregory T. Kavounas, Bellevue, WA (US)

(73) Assignee: West Affum Holdings Corp., Grand Cayman (KY)

( * ) Notice: Subject to any disclaimer, the term of this patent is extended or adjusted under 35 U.S.C. 154(b) by 0 days.

(21) Appl. No.: 16/147,450

(22) Filed: Sep. 28, 2018

(65) Prior Publication Data
US 2019/0143131 A1    May 16, 2019

Related U.S. Application Data

(60) Provisional application No. 62/584,659, filed on Nov. 10, 2017.

(51) Int. Cl.
*A61N 1/39*    (2006.01)
*A61N 1/04*    (2006.01)
*A61N 1/362*   (2006.01)

(52) U.S. Cl.
CPC ........... *A61N 1/3904* (2017.08); *A61N 1/046* (2013.01); *A61N 1/0484* (2013.01);
(Continued)

(58) Field of Classification Search
CPC ................ A61N 1/3904; A61N 1/0484; A61N 1/39–395
See application file for complete search history.

(56) References Cited

U.S. PATENT DOCUMENTS 3,724,355 A    4/1973 Unger
3,724,455 A    4/1973 Unger
(Continued)

FOREIGN PATENT DOCUMENTS

EP    3 233 185       6/2016
WO    1998039061 A2   9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Allen Porter
*Assistant Examiner* — Adreanne A. Arnold
(74) *Attorney, Agent, or Firm* — Spectrum IP Law Group LLC

(57) ABSTRACT

In embodiments, a Wearable Cardioverter Defibrillator (WCD) system includes a support structure for the patient to wear, and components that the support structure maintains on the patient's body. The components include a defibrillator, associated electrodes, and so on. The defibrillator can operate in a WCD mode while the patient wears the support structure. The defibrillator can further operate in a different, AED mode, during which time the patient need not wear a portion of the support structure, or even the entire support structure. Sometimes the AED mode is a type of a fully automatic AED mode. Other times the AED mode is a type of a semi-automated AED mode, where an attendant is
(Continued)

1+1:
PATIENT + ATTENDANT
(EMERGENCY EVENT)

present to administer the shock; at such times, the patient may not even need to have electrodes attached. This way the patient is more comfortable for a longer time.

22 Claims, 23 Drawing Sheets

(52) U.S. Cl.
CPC ......... *A61N 1/3625* (2013.01); *A61N 1/3918* (2013.01); *A61N 1/3925* (2013.01); *A61N 1/3968* (2013.01); *A61N 1/3987* (2013.01); *A61N 1/3993* (2013.01)

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,190 A | 8/1998 | Olson et al. |
| 5,792,204 A | 8/1998 | Snell |
| 5,855,592 A | 1/1999 | McGee et al. |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 F1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 10,449,378 B2 | 10/2019 | Kaib et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1* | 6/2012 | Kaib .................. A61N 1/0476 607/7 |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0052201 A1* | 2/2014 | Daynes ................. A61N 1/046 607/5 |
| 2014/0070957 A1 | 3/2014 | Longinotti-Buitoni et al. |
| 2014/0163663 A1 | 6/2014 | Poddar et al. |
| 2014/0207201 A1 | 7/2014 | Piha et al. |
| 2014/0243918 A1* | 8/2014 | Sullivan .............. A61N 1/3993 607/6 |
| 2014/0277226 A1* | 9/2014 | Poore .................. A61N 1/3987 607/7 |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0059023 A1* | 3/2016 | Freeman ............ A61N 1/36521 607/8 |
| 2016/0082277 A1 | 3/2016 | Foshee, Jr. et al. |
| 2016/0331987 A1 | 11/2016 | Chapman et al. |
| 2017/0266456 A1 | 9/2017 | Piha et al. |
| 2018/0243549 A1* | 8/2018 | Hill .................... A61B 5/6804 |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

European Search Report established Mar. 28, 2019, for EP application 18 205 426.2-1124.

Pagan-Carlo, et al., "Encircling Overlapping Multipulse Shock Waveforms for Transthoracic Defibrillation," JACC Journals, Dec. 1998, vol. 32 Issue 7, p. 2065-2071.

\* cited by examiner

SAMPLE COMPONENTS OF WEARABLE CARDIOVERTER DEFIBRILLATOR (WCD) SYSTEM

*PATIENT WEARING SAMPLE WCD*

*1+1:*
*PATIENT + ATTENDANT*
*(UNEVENTFUL TIMES)*

*1+1:*
*PATIENT + ATTENDANT*
*(EMERGENCY EVENT)*

SAMPLE COMPONENTS OF WEARABLE CARDIOVERTER DEFIBRILLATOR (WCD) SYSTEM CONVERTIBLE TO BE USED AS AN AED

*DEFIBRILLATION ELECTRODE*

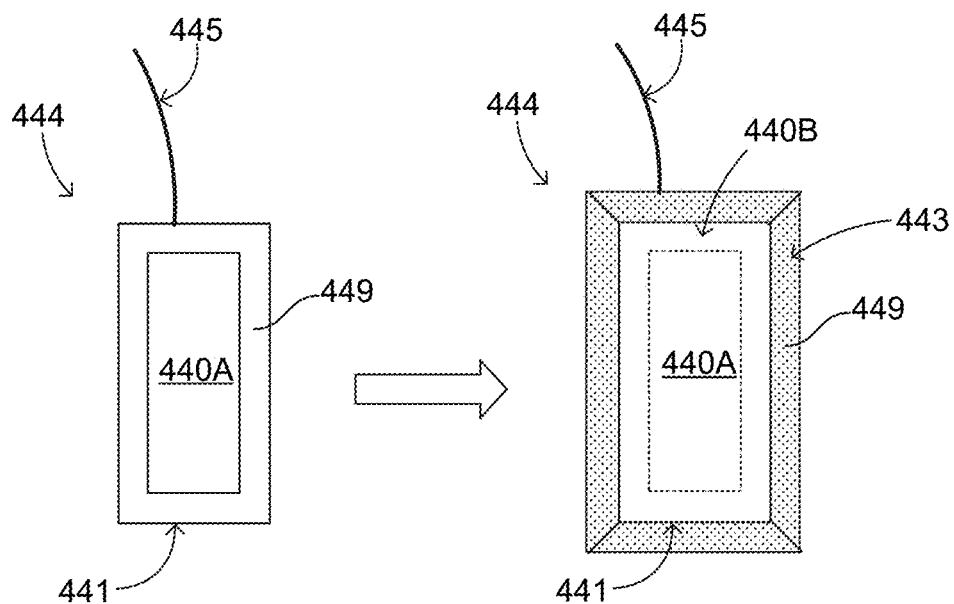
FIG. 4C
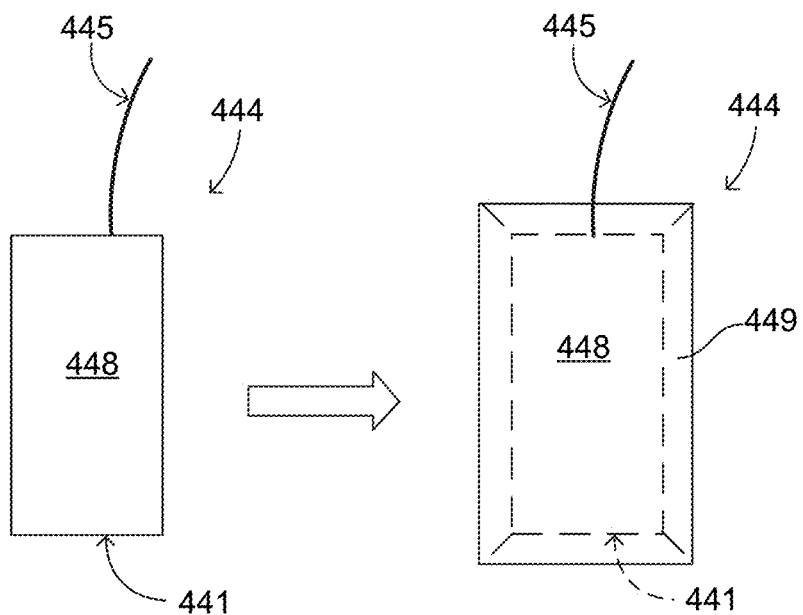
FIG. 4D  DEFIBRILLATION ELECTRODE WITH UNFOLDING ADHESIVE BACKER

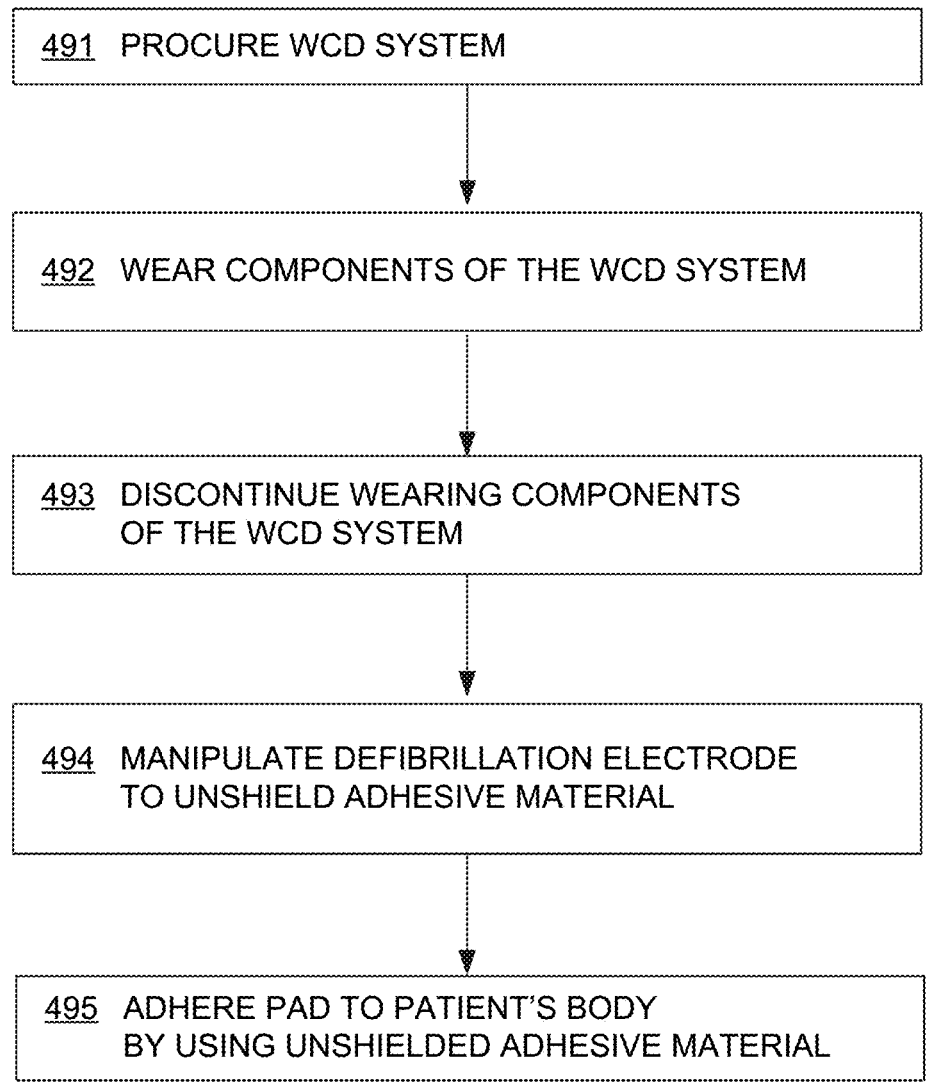

*1+1:
PATIENT + ATTENDANT
(UNEVENTFUL TIMES)*

*1+1:
PATIENT + ATTENDANT
(EMERGENCY EVENT)*

DEFIBRILLATOR PORTION USED WITH AED ELECTRODES

DEFIBRILLATOR PORTION USED WITH AED ELECTRODES

FIG. 8     *METHODS*

FIG. 9 — WCD SYSTEM WITH TWO POSSIBLE AED MODEs

*USER INTERFACE INDICATING CURRENT MODE*

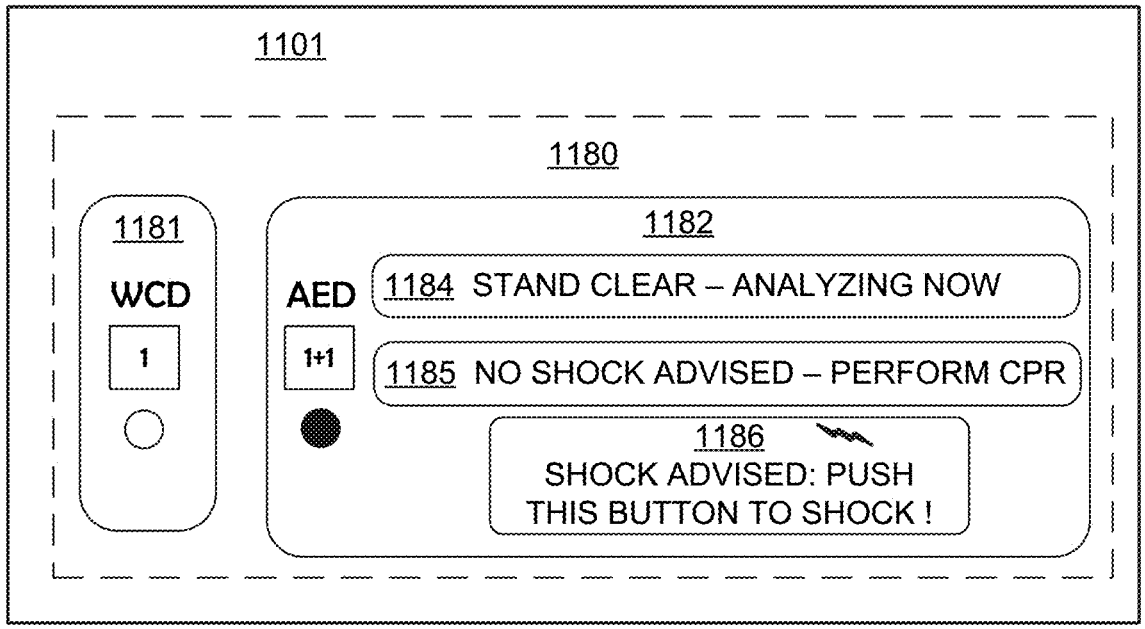
FIG. 11 — *USER INTERFACE FOR OPERATIONS OF WCD SYSTEM IN SEMI-AUTOMATIC AED MODE*
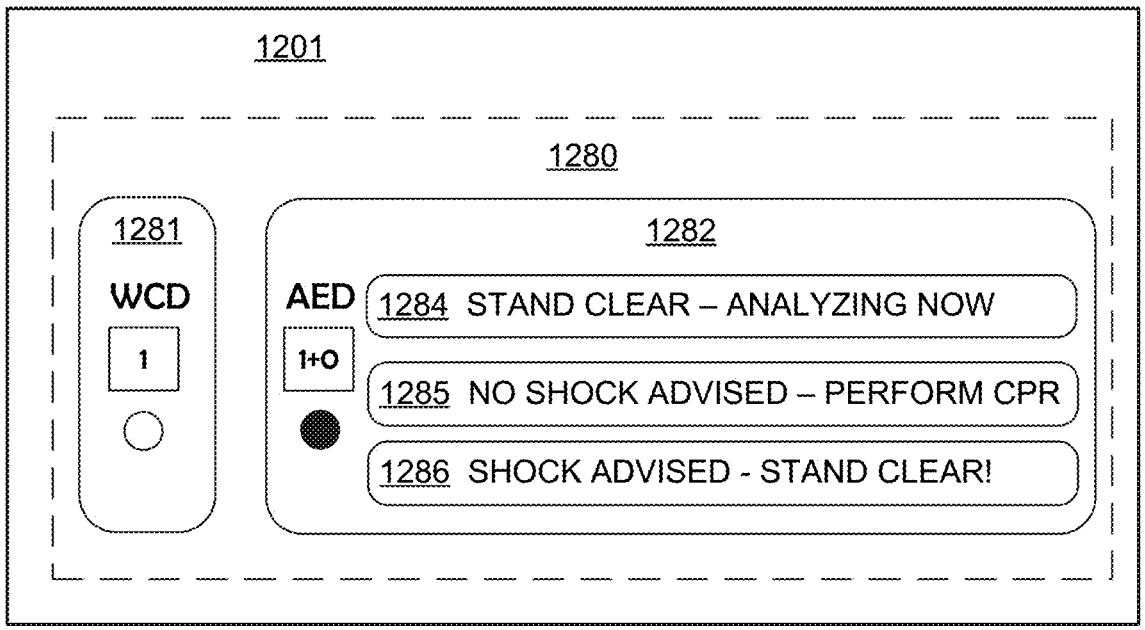
FIG. 12 — *USER INTERFACE INDICATING OPERATIONS OF WCD SYSTEM IN FULLY AUTOMATIC AED MODE*

*USER INTERFACE ENABLING
USER TO SELECT MODE*

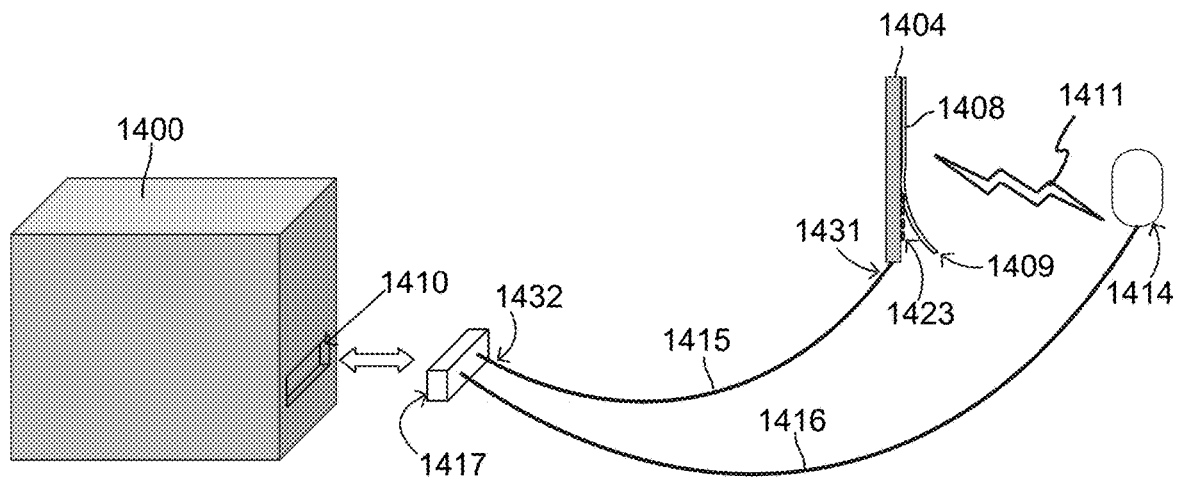
FIG. 14 *DEFIBRILLATOR WITH SAMPLE AED ELECTRODES HAVING EXTRA-LONG WIRE LEADS*
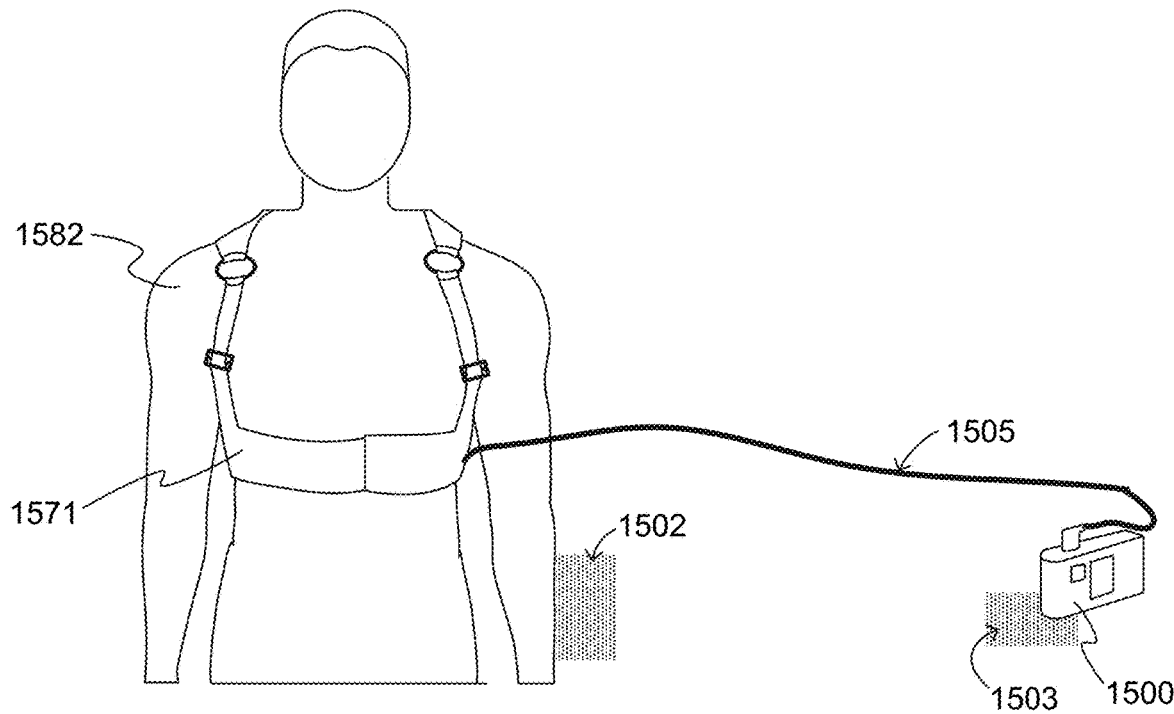
FIG. 15 *WCD SYSTEM WITH EXTRA-LONG CABLE(S)*

*WCD SYSTEM WITH WATERTIGHT COVER*

FIG. 18     *DAILY SCENARIOS*

SAMPLE COMPONENTS OF EXTERNAL DEFIBRILLATOR

SAMPLE COMPONENTS OF EXTERNAL DEFIBRILLATOR

WEARABLE CARDIOVERTER DEFIBRILLATOR (WCD) SYSTEM HAVING WCD MODE AND ALSO AED MODE

CROSS REFERENCE TO RELATED PATENT APPLICATIONS

This patent application claims priority from U.S. Provisional Patent Application Ser. No. 62/584,659, filed on Nov. 10, 2017.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

A challenge with wearing a Wearable Cardioverter Defibrillator (WCD) system is that it can feel uncomfortable for the patient to wear continuously for several weeks, as may have been prescribed. As such, patients sometimes simply do not wear it at some times, during which they are not protected by the WCD system.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of Wearable Cardioverter Defibrillator (WCD) systems, devices, storage media that may store programs, and methods, the use of which may help overcome problems and limitations of the prior art.

In embodiments, a Wearable Cardioverter Defibrillator (WCD) system includes a support structure for the patient to wear, and components that the support structure maintains on the patient's body. The components include a defibrillator, associated electrodes, and so on. The defibrillator can operate in a WCD mode while the patient wears the support structure. The defibrillator can further operate in a different, AED mode, during which time the patient need not wear a portion of the support structure, or even the entire support structure. Sometimes the AED mode is a type of a fully automatic AED mode. Other times the AED mode is a type of a semi-automated AED mode, where an attendant is present to administer the shock; at such times, the patient may not even need to have electrodes attached. This way the patient is more comfortable for a longer time.

In embodiments, a Wearable Cardioverter Defibrillator (WCD) system includes a support structure for the patient to wear, a defibrillator, at least one associated defibrillation electrode, and so on. The defibrillation electrodes includes a pad that can be coupled to the support structure so that the support structure maintains the pad on the patient's body when worn. The pad can also include an adhesive material arranged so that it is shielded when the electrode is used with the WCD system in the long term. If the patient has a cardiac emergency at a time that he is not wearing a support structure of the WCD system, a trained attendant may manipulate the defibrillation electrode to unshield the adhesive material, use the unshielded adhesive material to attach the electrode to the patient's body, and then use the defibrillator as an AED.

In embodiments, a defibrillation electrode has a pad that presents two opposite conductive surfaces. The first surface is exposed, and can be used in a Wearable Cardioverter Defibrillator (WCD) system that a patient wears in the long term. The second surface has adhesive. If the patient has a cardiac emergency at a time that he is not wearing a support structure of the WCD system, a trained attendant may attach the pad to the patient by the pad's second surface via the adhesive material. In some embodiments that second surface is originally further provided with a liner, which the attendant can first remove to expose the adhesive material. Then the attendant may use a defibrillator of the WCD system in an AED mode. This electrode thus helps enable the patient to spend significant amounts of time without needing to wear or carry any components of the WCD system.

In embodiments, a defibrillation electrode has a pad with a first conductive surface and a second surface. A back layer has a main portion covering the second surface, and an end portion that can cover a covered portion of the first surface, while leaving another portion of the first surface exposed. An adhesive material can maintain the end portion on the covered portion. The electrode can therefore be used with a Wearable Cardioverter Defibrillator (WCD) system, by using the exposed portion to contact the patient in the long term. If the patient has a cardiac emergency while not wearing the WCD system, an attendant can peel the end portion from the covered portion to expose the adhesive material of the electrode, use the adhesive material to attach the pad to the patient, and use the defibrillator of the WCD system in an AED mode.

In embodiments, a Wearable Cardioverter Defibrillator (WCD) system includes a support structure for the patient to wear, and components that the support structure maintains on the patient's body. The components include a defibrillator, associated electrodes, and so on. The defibrillator is useable also with different, separate AED electrodes, which permits the patient to spend significant amounts of time without wearing the support structure. Sometimes the defibrillator can further operate in a different, AED mode that is a type of a fully automatic AED mode. Other times the AED mode is a type of a semi-automated AED mode, where an attendant is present; at those times, the patient may not even need to have electrodes attached. This way the patient is more comfortable for a longer time, while remaining protected by the WCD system.

In embodiments, a defibrillator system includes a defibrillator, and electrode pads that are coupled to the defibrillator via wire leads. The wire leads can be extra-long, for example longer than 5 ft (152 cm). A patient who needs a Wearable Cardioverter Defibrillator (WCD) system can remain protected for some time by turning on the defibrillator and maintaining the electrode pads on their body, whether by adhesive attachment or by using only a portion of the support structure of the WCD system. Accordingly, when the patient is not moving around much, such as while sitting in a semi-private setting or sleeping, the patient may spend significant amounts of time burdened by less than the full weight of the WCD system, specifically without needing to carry the defibrillator, or wear the entire support structure of the WCD system, or even wear any portion of that support structure.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 4C shows plan views of the front side a sample electrode according to embodiments that have a back layer, before and after an end portion of the back layer is unfolded to expose adhesive material.

FIG. 4D shows plan views of back sides of the plan views of FIG. 4C.

FIG. 4E is a flowchart for illustrating sample methods according to embodiments.

FIG. 11 is a diagram of a sample user interface that indicates operations of a defibrillator of a WCD system at a moment that it is operating in a semi-automatic AED mode according to embodiments.

FIG. 12 is a diagram of a sample user interface that indicates operations of a defibrillator of a WCD system at a moment that it is operating in a fully automatic AED mode according to embodiments.

FIG. 14 is a diagram of a defibrillator that uses sample AED electrodes having extra-long wire leads according to embodiments.

FIG. 15 is a diagram of a patient wearing a sample WCD system that uses an extra-long cable according to embodiments.

DETAILED DESCRIPTION

As has been mentioned, the present description is about Wearable Cardioverter Defibrillator (WCD) systems, devices, storage media that may store programs, and methods. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
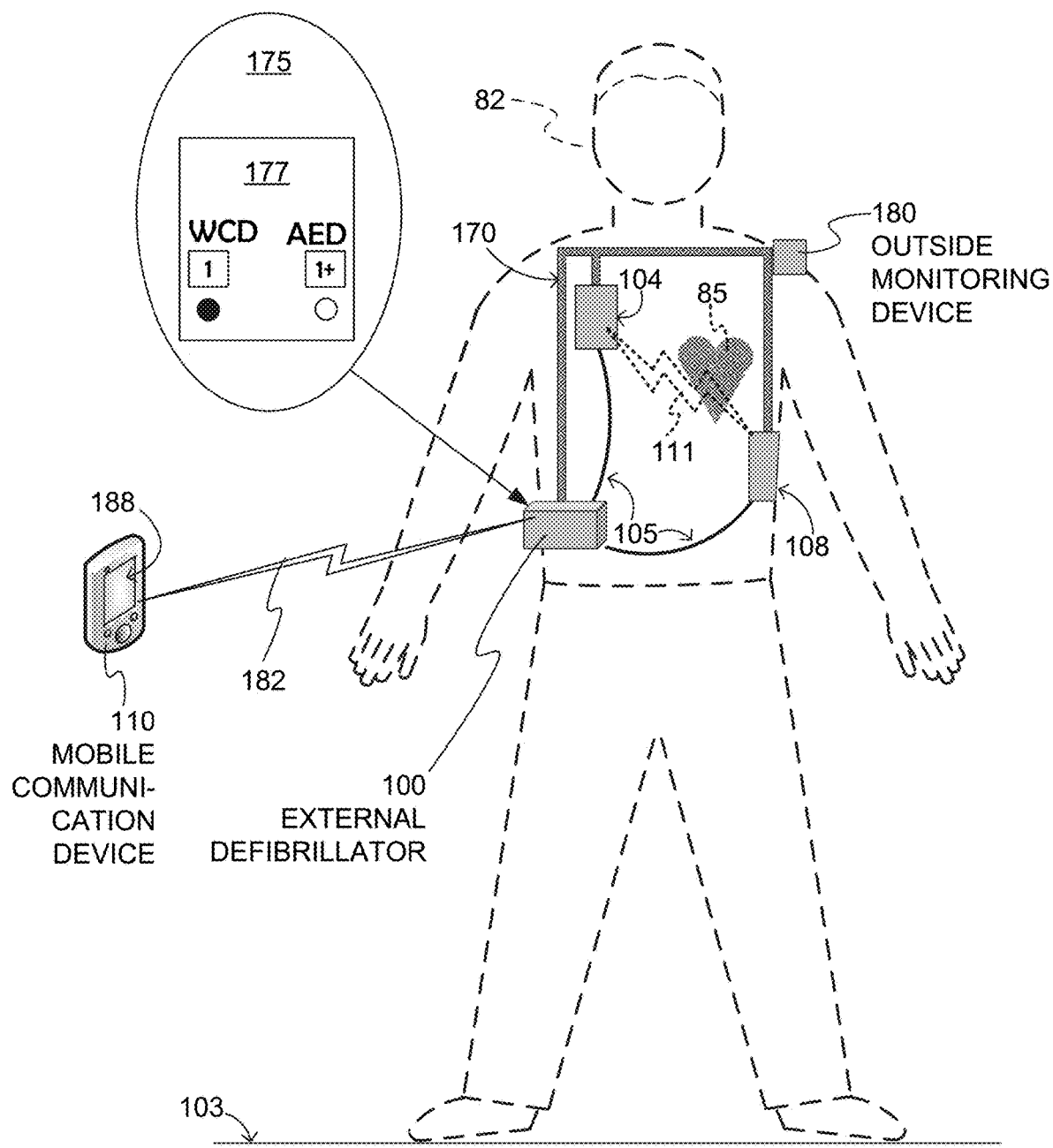
FIG. 1 is a is a diagram of components of a sample wearable cardioverter defibrillator (WCD) system which, while worn by the patient, is operating in a WCD mode according to embodiments.

FIG. 1 depicts a patient 82 standing on a floor 103. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. That is, for example, a user of the wearable cardioverter defibrillator (WCD) may also be a clinician such as a doctor, nurse, emergency medical technician (EMT) or other similarly situated individual (or group of individuals). In some situations, a user can be an attendant who is committed to patient 82, in which case patient 82 is overseen by the attendant. Instances of a sample attendant 83 can be seen in later drawings, such as FIGS. 3A, 3B, 5A, 5B, and so on. In some cases, a user may be a bystander, for example if a planned attendant is absent for some reason. The particular context of these and other related terms within this description should be interpreted accordingly.

Remaining with FIG. 1, a WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105, which can also be called wire leads and simply leads. Defibrillation electrodes 104, 108 can be configured to be worn by patient 82 in a number of ways. For instance, defibrillator 100 and defibrillation electrodes 104, 108 can be coupled to support structure 170, directly or indirectly. In some embodiments, defibrillation electrodes 104, 108 can be configured to be uncoupled from support structure 170, by un-attaching them, removing them from pockets of a vest, etc. As such, support structure 170 can be configured to be worn by ambulatory patient 82 so as to maintain at least one of electrodes 104, 108 on the body of ambulatory patient 82, while patient 82 is moving around, etc. Of course, by this it is meant that at least the pads of the electrodes are maintained on the body, because the electrical discharge will take place through the pads. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In the embodiment of FIG. 1, defibrillator 100 is communicatively coupled with a mobile communication device 110 via a communication link 182. Mobile communication device 110 can be implemented as a cellphone, a laptop, a portable device custom to the WCD system of FIG. 1, and so on. Mobile communication device 110 includes a user interface 188, which can also perform the functions of a user interface of a system described later in this document.

In embodiments, defibrillator 100 and/or its processor inside can be in different modes. According to a comment 175, an indicator 177 indicates that defibrillator 100 is in a WCD mode, and not in an AED mode. Indicator 177 is used in this document for purposes of describing the state of defibrillator 100 and/or its processor in the example of FIG. 1. The mode may be implemented as different states of a state machine of a processor, a logical flag, etc. A user interface may show to a user the current mode, and so on, as described later in this document. For a WCD mode, the acronym "WCD" is explained above. For an AED mode, the acronym "AED" stands for Automated External Defibrillator, of the type known in the art. An example is described in U.S. Pat. No. 9,775,566, which incorporated in this document by reference.

Moreover, for indicating the mode, a conceptual notation is used in the drawings of this document. In this notation, where "1" is associated with the WCD mode, and "1+" is associated with an AED mode, when no particular AED mode is specified and any AED mode would work. Moreover, "1+1" is associated with an AED mode that requires an attendant present, and "1+0" is associated with an AED mode that does not require an attendant present. These different modes are further contrasted in FIG. 18, whose description appears later in this document.

Remaining with FIG. 1, in some embodiments a processor of defibrillator 100 is configured to determine, from the patient input of ECG, or motion etc., whether or not a first shock criterion is met. The processor can then be further configured to cause, responsive to the first shock criterion being met, at least some of the stored electrical charge to be discharged via electrode 104 through patient 82 so as to deliver a first shock to patient 82. For purposes of this description, shock 111 can be considered to be first shock, delivered while by the WCD is operating in the WCD mode.

There are a number of possible embodiments for the WCD system of FIG. 1. Examples are now described.

Figure 2:
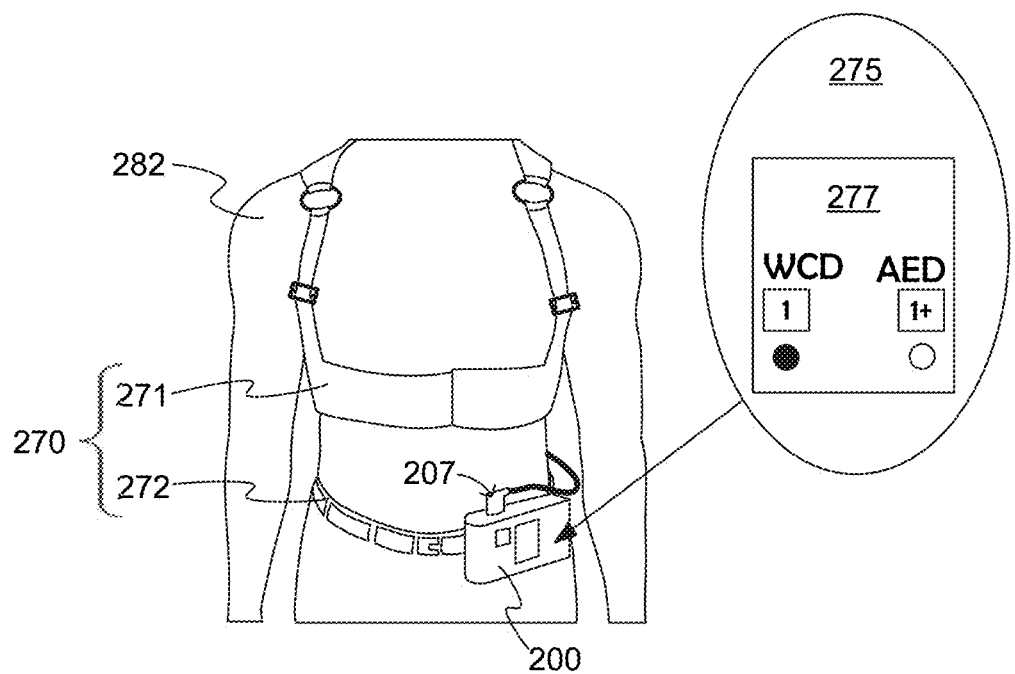
FIG. 2 is a diagram showing a sample embodiment of the WCD system of FIG. 1.

FIG. 2 is a diagram showing a sample non-generic embodiment of the WCD system of FIG. 1. The torso of a patient 282 is shown. Patient 282 is wearing a support structure 270 that includes an upper vest 271 and a belt 272 that is worn on the waist. A defibrillator 200 is supported by belt 272. The electrodes are held in place by upper vest 271 against the patient's torso, and terminate in a plug 207 that is plugged into a socket of defibrillator 200. According to a comment 275, an indicator 277 indicates that defibrillator 200 is in the WCD mode, as opposed to an AED mode. Patient 282 is ambulatory, moving around while being protected by the WCD system, and so on. Patient 282 may further wear clothes that cover the WCD system, which gives patient 282 more privacy and dignity while in public.

Figure 3A:
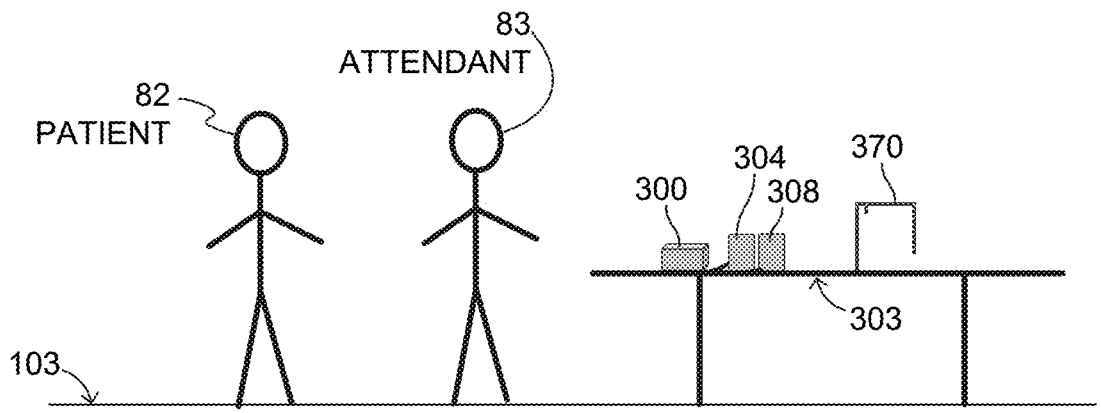
FIG. 3A is a diagram of a sample scene of a patient and an attendant, at a time when the patient is not wearing a sample WCD system that is made according to embodiments.

FIG. 3A is a diagram of a sample scene of patient 82 and an attendant 83. Attendant 83 may be a trained person such as a nurse, a trusted family member, and so on.

Patient 82 has an embodiment of a WCD system, which he is not wearing at all at that time so as to be more comfortable. In particular, patient 82 has taken off the components of his WCD system, and has left them on a nearby table 303. These components include a support structure 370, a defibrillator 300, electrodes 304, 308, etc., which can be as described respectively for support structure 170, defibrillator 100, electrodes 104, 108, and so on. This is also a good opportunity to clean support structure 170. For example, if support structure 170 includes a vest, the scenario of FIG. 3A is a good opportunity to launder it, etc.

In FIG. 3A, defibrillator 300 may be either in the WCD mode or an AED mode. If patient 82 experiences no event— as will likely happen in the vast majority of the days during which the patient needs to wear the WCD system—patient 82 will have managed to spend hours and days of not wearing the WCD system, as long as attendant 83 remains close and attentive. At any time, if patient 282 starts to feel unwell, he may put back on the WCD system. In those cases, a processor of defibrillator 300 may operate as in the WCD mode of FIG. 1, namely determine, from the patient input, whether or not a first shock criterion is met and, if so, cause at least some of the stored electrical charge to be discharged via WCD electrodes 304, 308 through patient 82, so as to deliver a first shock to patient 82 when support structure 370 is worn by patient 82.

Figure 3B:
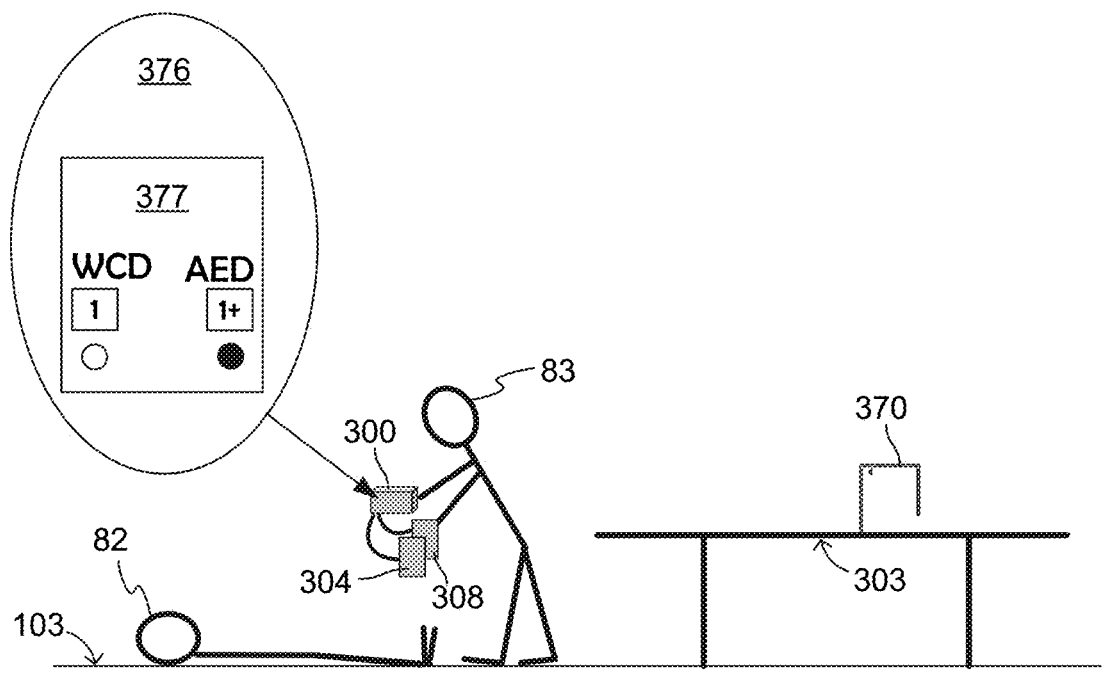
FIG. 3B is a diagram of a sample scene that can result from the scene of FIG. 3A, where the patient is having a cardiac emergency, and the attendant is using the WCD system in an AED mode together with the defibrillation electrodes of the WCD system, according to embodiments.

FIG. 3B is a diagram of a sample scene that can result from the scene of FIG. 3A, where patient 82 is having an unexpected cardiac emergency event, and is lying on floor 103 without having had the opportunity to put on the WCD system. Attendant 83 has taken defibrillator 300 and electrodes 304, 308 and is using them to treat patient 82. In the sample scene of FIG. 3B, attendant 83 has left the entire support structure 370 on table 303, although other embodiments are possible.

In the sample scene of FIG. 3B, attendant 83 is using these components similarly to how one would use an AED. In particular, the WCD system further includes a user interface, examples of which are described elsewhere in this document. The user interface may include a shock input device that is configured to receive a shock input. The user interface may further advantageously include one or more output devices that can emit human-perceptible indications, as described later in this document. Such a shock input may be entered by attendant 83, to cause a shock to be delivered. In such embodiments, the processor of defibrillator 300 can be further configured to cause, responsive to the shock input being received, at least some of the stored electrical charge to be discharged via the first electrode 304 through the patient so as to deliver a second shock to the patient. This second shock can be distinct from the first shock, in that the second shock is administered in the AED mode, while the first shock mentioned above was administered in the WCD mode. Indeed, at the time of FIG. 3B, according to a comment 376, an indicator 377 indicates that defibrillator 300 is now in an AED mode, and no longer in a WCD mode such as the WCD mode indicators 177, 277.

In such embodiments, a number of features are notable. To begin with, in the WCD mode the WCD system may emit a noise alarm if the ECG signal is too noisy to allow analysis, and a "shock imminent" alarm if a shockable rhythm is detected. Also, the electrodes in the sample scene of FIG. 3B may be placed on the patient's chest, and not in the anterior-posterior position that support structure 170 of FIG. 1 may implement. Moreover, when the second shock is delivered, patient 82 is not wearing at least a portion of support structure 370. In fact, in the sample embodiment of FIG. 3B, when the second shock is delivered patient 82 is not wearing any portion of support structure 370. In addition, the second shock in the AED mode can be delivered when electrodes 304, 308 are uncoupled from support structure 370. This, however is not required.

It will be appreciated that the second shock in AED mode can be a shock for a variety of purposes that are similar to the first shock. For example, the second shock can be a defibrillation shock with energy higher than 50 Joule (J), for example 200 J, 360 J, etc. Or, the second shock can be a pacing shock with energy of at most 20 J, such as 10 J, 5 J, etc.

For the embodiments of FIG. 3A, 3B, it will be appreciated that defibrillator 300 is not an ordinary AED, but is a WCD that is further adjusted to operate either in a WCD mode, or in one or more AED modes. An ordinary AED could not easily function as the defibrillator of a WCD system for a number of reasons. To name a few such reasons, an ordinary AED has the benefit of an attendant who controls the scene, without having to anticipate scenarios of the patient, such as solitary driving, or of bystanders who do not recognize that a high-power shock will be delivered. Further, an ordinary AED has the benefit of a patient who is motionless, and on whom the electrodes are applied well. As such, an AED receives an ECG signal that neither has no spurious components from motion of the patient, nor is affected by electrical noise from friction of the electrodes against the body of the patient.

Moreover, embodiments provide options for attendant 83 to attach electrodes 304, 308 to patient 82 without the help of support structure 370. Examples are now described.

Figure 4A:
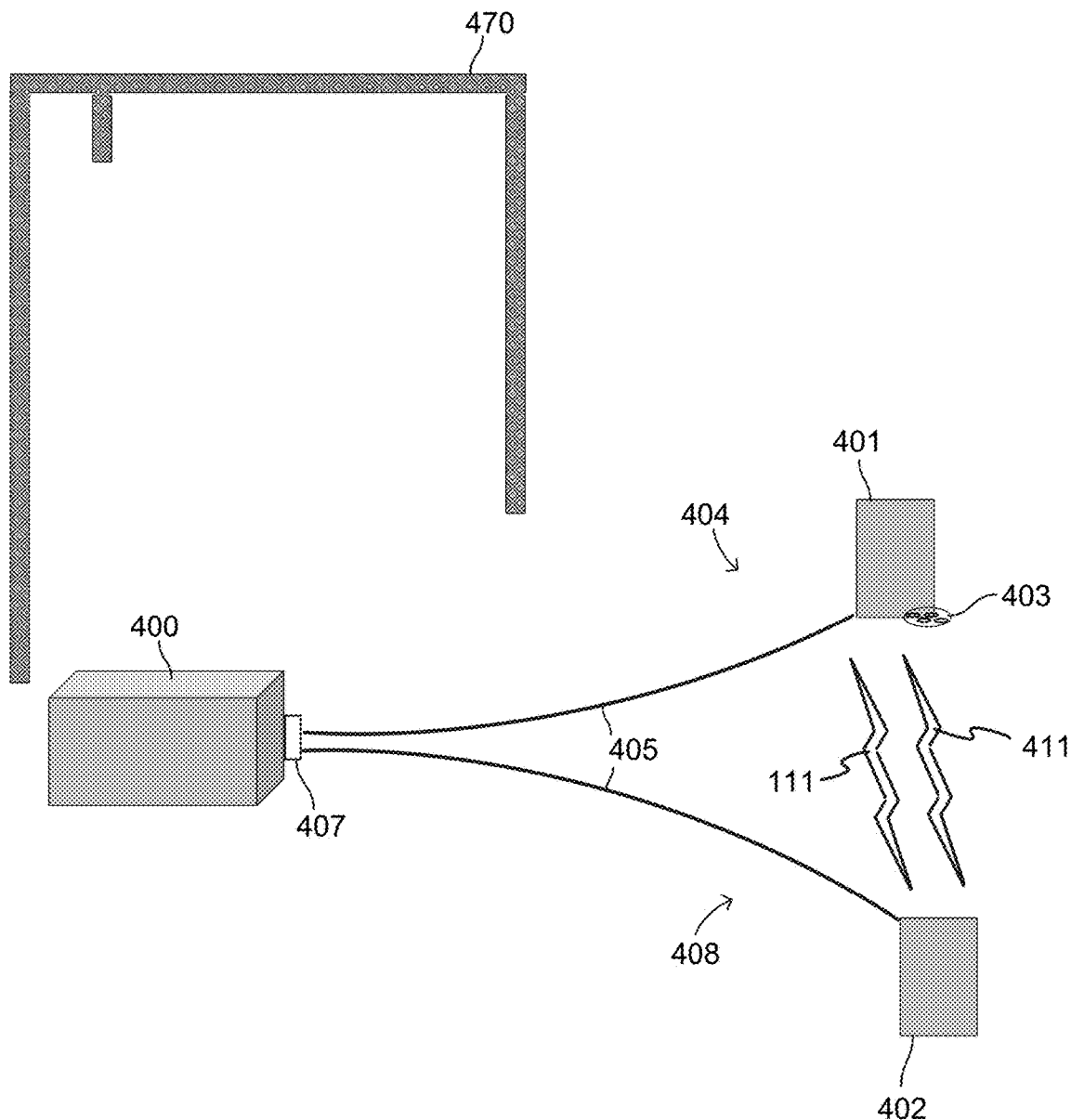
FIG. 4A is a diagram of components of a sample wearable cardioverter defibrillator (WCD) system that can be used for the examples of FIGS. 3A & 3B according to embodiments.

FIG. 4A is a diagram of components of a sample wearable cardioverter defibrillator (WCD) system that can be used for the examples of FIGS. 3A & 3B according to embodiments. These components include a support structure 470, which can be as support structure 170, and a defibrillator 400 that can be as defibrillator 100 and further configured to be coupled to support structure 470.

These components also include two defibrillation electrodes 404, 408. The earlier described first shock 111 and second shock 411 are delivered by discharges between the two electrodes, after these electrodes have been applied to the patient (not shown).

Defibrillation electrode 404 includes a wire lead 405 that is configured to be coupled to defibrillator 400. In this sample embodiment, defibrillation electrode 404 further includes a plug 407 at an end of wire lead 405. Plug 407 is configured to be coupled to defibrillator 400, for example in a socket.

Defibrillation electrodes 404, 408 further include electrode pads 401, 402. Pads 401, 402 can be coupled to respective leads 405. Pad 401, and also often pad 402, can be configured to be coupled to support structure 470 so that pad 401 is maintained on a body of the patient when support structure 470 is worn by the patient.

Defibrillation electrode 404, and optionally also defibrillation electrode 408, further includes an adhesive material 403. Adhesive material 403 can be arranged on the pad so that it is shielded from contacting support structure 470 or the body of the patient when pad 401 is thus maintained on the body of the patient by support structure 470. As such, while the WCD system is used in the WCD mode, pad 401 operates to deliver shock 111, with adhesive material 403 not playing a role.

For instance, pad 401 may be attached to support structure 470 removably, for example by snaps and so on. For such attachment, support structure 470 can have an internal pocket with holes, for example the pocket can be made out of a mesh structure. Pad 401 can be placed in the internal pocket, with an exposed surface facing the patient via the holes. Any released gel may fill in gaps, and so on.

In embodiments, defibrillation electrode 404 is further configured to be manipulated so as to enable the adhesive material to contact the body of the patient. In other words, the manipulation can discontinue the shielding of adhesive material 403. This manipulating can be performed by attendant 83, for example manually. As such, adhesive material 403 can be used to adhere pad 401 to the body of the patient for the AED mode of FIG. 3B. In such a case, support structure 470 may no longer be needed.

There are a number of possibilities for electrodes for the WCD system of FIG. 4A. In some embodiments, the adhesive material is on the pad. In some embodiments, defibrillation electrode 404 further includes a liner (not shown in FIG. 4A) attached to pad 401 via adhesive material 403, and manipulating includes removing the liner from pad 401. An example is now described.

Figure 4B:
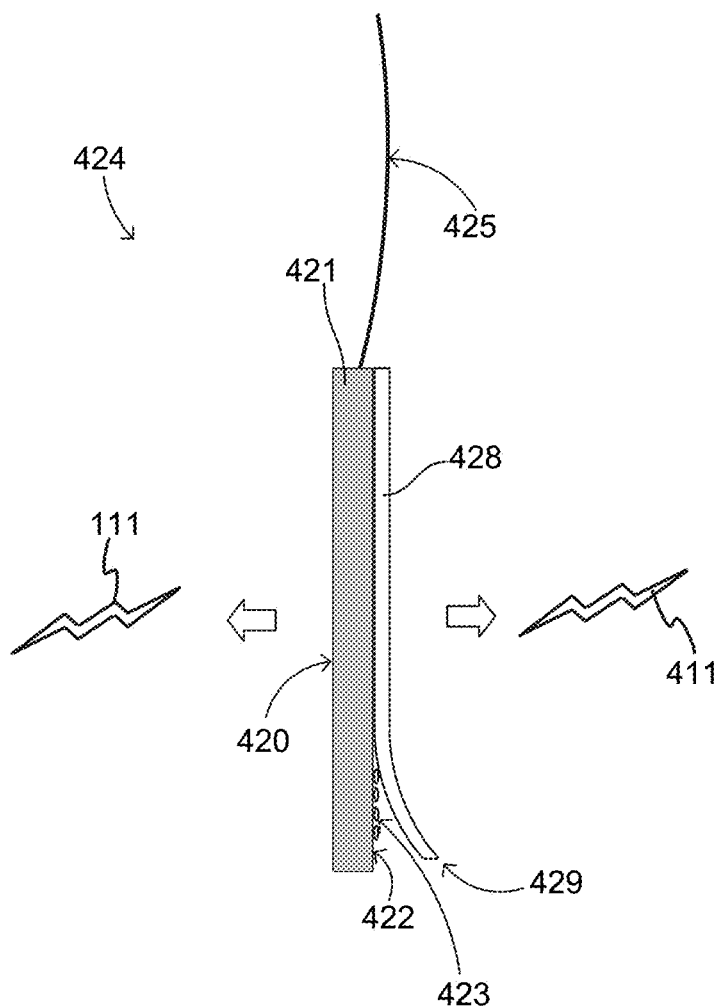
FIG. 4B is a side view of a sample embodiment of an electrode for the WCD system of FIG. 4A.

Referring to FIG. 4B, in some embodiments, a defibrillation electrode has a pad that presents two opposite surfaces, with one of them having adhesive material. In particular, a defibrillation electrode 424 includes a wire lead 425, and a pad 421 that is coupled to wire lead 425, and preferably is attached to wire lead 425. Pad 421 can be flexible or not.

Pad 421 presents a first conductive surface 420 that is exposed for contacting the patient, after it has been removed from its shipping container. Surface 420 can be used in WCD mode to be pressed against patient 82, so as to deliver first shock 111. Pad 421 further presents a second conductive surface 422, which is opposite first conductive surface 420. First and second conductive surfaces 420, 422 can be electrically coupled to wire lead 425. In one embodiment, pad 421 is a flat metal piece in electrical connection with wire lead 425, and its two opposite sides are conductive surfaces 420, 422.

Second conductive surface 422 can be used for delivering second shock 411 in the AED mode. In some embodiments, there is an adhesive material 423 on second conductive surface 422, while there may be no adhesive material on first conductive surface 420. In such embodiments, adhesive material 423 is used for attaching second conductive surface 422 of pad 421 to the body of patient 282.

In some embodiments, electrode 424 further includes a liner 428 attached to second conductive surface 422. Liner 428 may be so attached via adhesive material 423. Liner 428 may be so attached removably, where removing may be performed by peeling liner 428 from its edge 429. It will be recognized that liner 428 is an example of a shield for the shielding, and peeling is an example of manipulating electrode 424 to unshield.

As such, while defibrillator 400 operates in the WCD mode, pad 421 can be used with its exposed surface 420 facing the patient, for delivering first shock 111. During such times, liner 428 may shield adhesive material 423 on side 422 from contacting and/or adhering to support structure 470 or to the body of the patient. And, for operating defibrillator 400 in the AED mode during the emergency scene of FIG. 3B, liner 428 can be removed, and pad 421 can be attached directly to the patient by the adhesive material 423. The second surface of pad 421, with adhesive material 423 and liner 428 can be implemented as is known for AED electrodes. In other embodiments for the WCD system of FIG. 4A, defibrillation electrode 404 further includes a backer with an end portion that is folded onto pad 401, and manipulating includes removing that end portion of the backer from pad 401. An example is now described.

Referring now to FIGS. 4C and 4D, an electrode 444 has a wire lead 445 and a pad 441 that coupled to wire lead 445, and preferably is attached to wire lead 445. Pad 441 can be flexible or not.

Pad 441 presents a first conductive surface that has an exposed portion 440A and an initially covered portion 440B. Pad 441 further presents a second surface opposite the first surface.

Electrode 444 also has a back layer with has a main portion 448 attached to the second surface of pad 441, which is why the second surface does not appear directly in these diagrams. The back layer also has an end portion 449 that extends past pad 441, and can be wrapped around and folded over so as to further cover a covered portion 440B of the first surface. End portion 449 need not cover an exposed portion 440A of the first surface. Electrode 444 can therefore be used with a WCD system in the WCD mode, by using exposed portion 440A to protect the patient in the long term.

Electrode 444 can further have an adhesive material 443 between covered portion 440B of the first surface and end portion 449 of the back layer. In fact, adhesive material 443 can maintain end portion 449 adhered to covered portion 440B.

End portion 449 can be configured to be peeled from covered portion 440B of the first surface and unfolded. Peeling and unfolding may expose adhesive material 443, which can be used for attaching pad 441 to patient 82. This peeling and unfolding is another example of manipulating electrode 424.

In the example of FIG. 4C, adhesive material 443 is provided only on end portion 449 of the back layer, but that is not necessary. Alternately or additionally, adhesive material can be provided on the initially covered portion 440 of the first surface.

This description also includes methods.

FIG. 4E shows a flowchart 490 for describing methods according to embodiments. According to an operation 491, a WCD system is procured that is intended for an ambulatory patient. The WCD system may including a support structure, a defibrillator, a defibrillation electrode including a wire lead, a pad, and an adhesive material arranged on the pad. If disassembled, the WCD system may be as described for FIG. 4A.

According to another operation 492, components of the WCD system may be worn by the ambulatory patient. For example, the support structure is worn, with the defibrillator coupled to the support structure, the pad coupled to the support structure so that the pad is maintained on a body of the patient, the wire lead coupled to the pad and to the defibrillator, and the adhesive material is shielded from contacting the support structure or the body of the patient. The adhesive material may be so shielded by how it is initially arranged on the pad.

According to another operation 493, wearing of the support structure is discontinued. In some embodiments, this discontinuing includes uncoupling the defibrillator from the support structure, uncoupling the defibrillation electrodes from the support structure, etc.

According to another, optional operation 494, the defibrillation electrode may be manipulated as already mentioned above. Manipulating may include unshielding the adhesive material, and thus permitting it to contacting the body of the patient. This operation may be performed by the patient or an attendant. Of course, unshielding means the opposite of shielding.

According to another operation 495, the pad may be adhered to the body of the patient by using the adhesive material. This way the defibrillator of the WCD system is ready for use as an AED, for example as shown in FIG. 3B. This operation may be performed by the patient or an attendant.

In some embodiments, a WCD system is useable with WCD electrodes and also with AED electrodes. In such embodiments, AED electrodes may be provided in addition to the WCD electrodes that are used when the patient is normally wearing the entire WCD system, such as in the example of FIG. 1. Examples are now described.

Figure 5A:
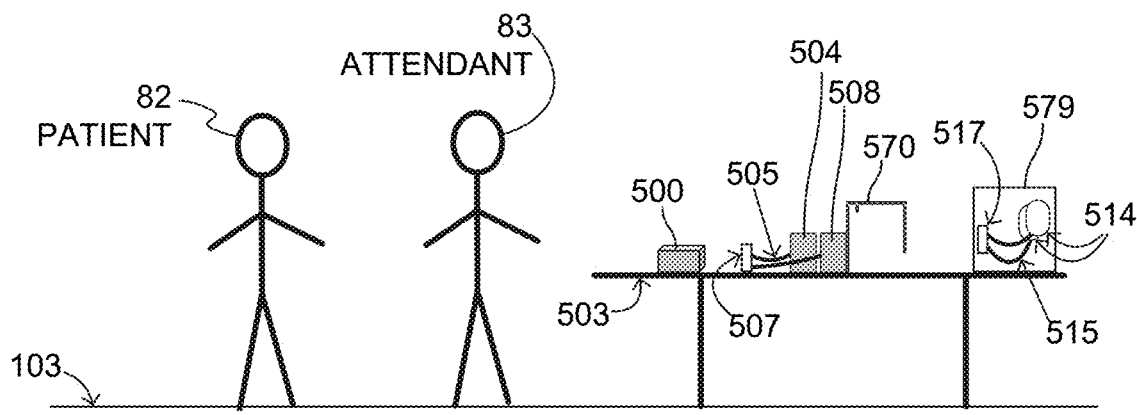
FIG. 5A is a diagram of a sample scene of a patient and an attendant, at a time when the patient is not wearing a sample WCD system that is made according to embodiments.

FIG. 5A is a diagram of a sample scene of patient 82 and an attendant 83. Patient 82 has an embodiment of a WCD system, which he is not wearing at all at the time, so as to be more comfortable. In particular, patient 82 has taken off the components of his WCD system, and has left them on a nearby table 503. These components include a support structure 570, a defibrillator 500, electrodes 504, 508, wire leads 505, which can be as described respectively for support structure 170, defibrillator 100, a set of electrodes 104, 108, and wire leads 105. Wire leads 505 come together in a single plug 507, which has been unplugged from a socket of defibrillator 500.

In addition, the components include a set of AED electrodes. In particular, an unopened package 579 includes a set of AED electrodes that have pads 514, and also have leads 515 that terminate in a single plug 517. Pads 514 can be made differently from the pads of electrodes 504, 508. For example, pads 514 may include adhesive material, and be configured to be maintained on the body of patient 82 via the adhesive material, similarly with how it is done with AED electrodes known in the art. The AED electrodes can be configured to be coupled to the housing of defibrillator 500, for example by having plug 517 be received in a socket of defibrillator 500.

In FIG. 5A, as with FIG. 3A, defibrillator 500 may be either in the WCD mode or an AED mode. Patient 82 may have stopped wearing support structure 570 after returning home from outside. Patient 82 may be reading the newspaper, eating dinner without moving around much, and so on, while attendant 83 remains close. At any time, if patient 282 starts feeling unwell, he may put back on the WCD system. In those cases, a processor of defibrillator 500 may operate as in the WCD mode of FIG. 1, namely determine, from the patient input, whether or not a first shock criterion is met and, if so, cause at least some of the stored electrical charge to be discharged via WCD electrodes 504, 508 through patient 82, so as to deliver a first shock to patient 82 when support structure 570 is worn by patient 82. This first shock, however, will not be via the set of AED electrodes in package 579.

Figure 5B:
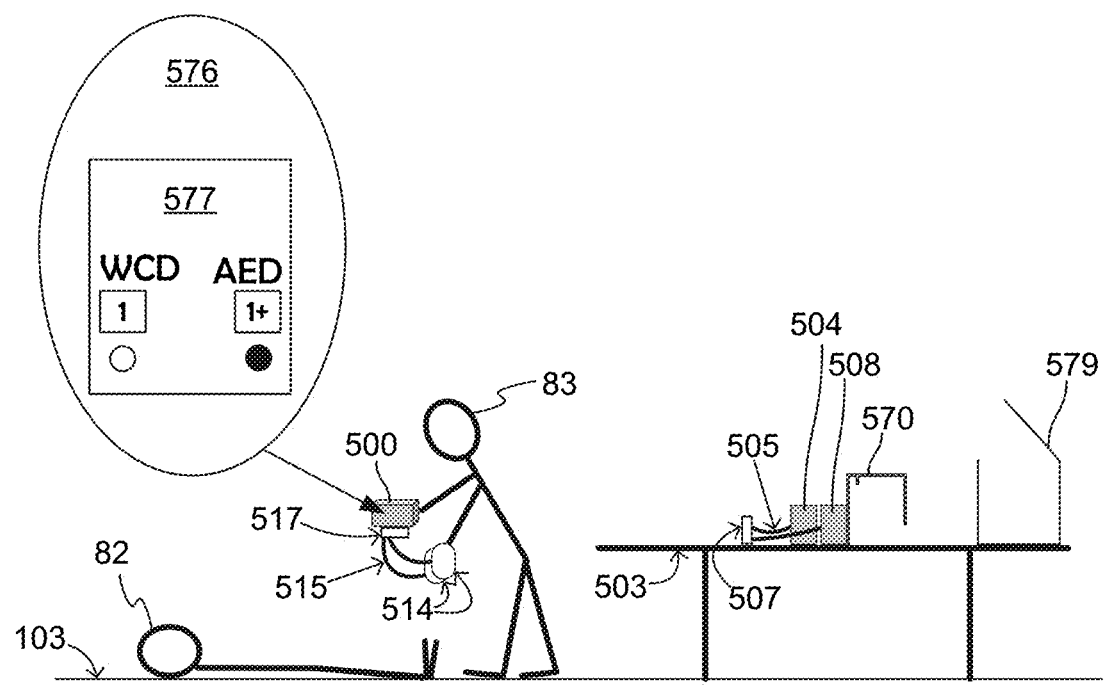
FIG. 5B is a diagram of a sample scene that can result from the scene of FIG. 5A, where the patient is having a cardiac emergency, and the attendant is using the WCD system in an AED mode together with separate AED defibrillation electrodes, according to embodiments.

FIG. 5B is a diagram of a sample scene that can result from the scene of FIG. 5A, where patient 82 is having an unexpected cardiac emergency event, and is lying on floor 103 without having had the opportunity to put on the WCD system. Attendant 83 has opened package 579, has taken from it the set of AED electrodes, and has plugged plug 517 of the AED electrodes into defibrillator 500. Attendant 83 is further using defibrillator 500 with the AED electrodes to treat patient 82. In the sample scene of FIG. 5B, attendant 83 has left on table 503 the opened package 579 that is now empty, the entire support structure 570, and the WCD electrode set 504, 508, although other embodiments are possible.

In the sample scene of FIG. 5B, attendant 83 is using these components similarly to how one would use an AED. In particular, the WCD system further includes a user interface, examples of which are described elsewhere in this document. The user interface may include a shock input device that is configured to receive a shock input. Such a shock input may be entered by attendant 83, to cause a shock to be delivered. In such embodiments, the processor of defibrillator 500 can be further configured to cause, responsive to the shock input being received, at least some of the stored electrical charge to be discharged via the AED electrodes through patient 82 so as to deliver a second shock to patient 82. This second shock can be distinct from the first shock, in that the second shock is administered in the AED mode, while the first shock was mentioned above was administered in the WCD mode. Indeed, at the time of FIG. 5B, according to a comment 576, an indicator 577 indicates that defibrillator 500 is now in an AED mode, and no longer in a WCD mode such as the WCD mode indicators 177, 277. As such, the second shock was not through WCD electrodes 504, 508.

In such embodiments, a number of features are notable. First, when the second shock is delivered, patient 82 is not wearing any portion of support structure 570. In addition, WCD electrodes 504, 508 can be configured to be uncoupled from the housing of defibrillator 500, so they can be advantageously left on table 503. This, however is not required.

Defibrillator 500 can accommodate and operate with wholly different sets of electrodes. Two sample embodiments are now described.

Figure 6:
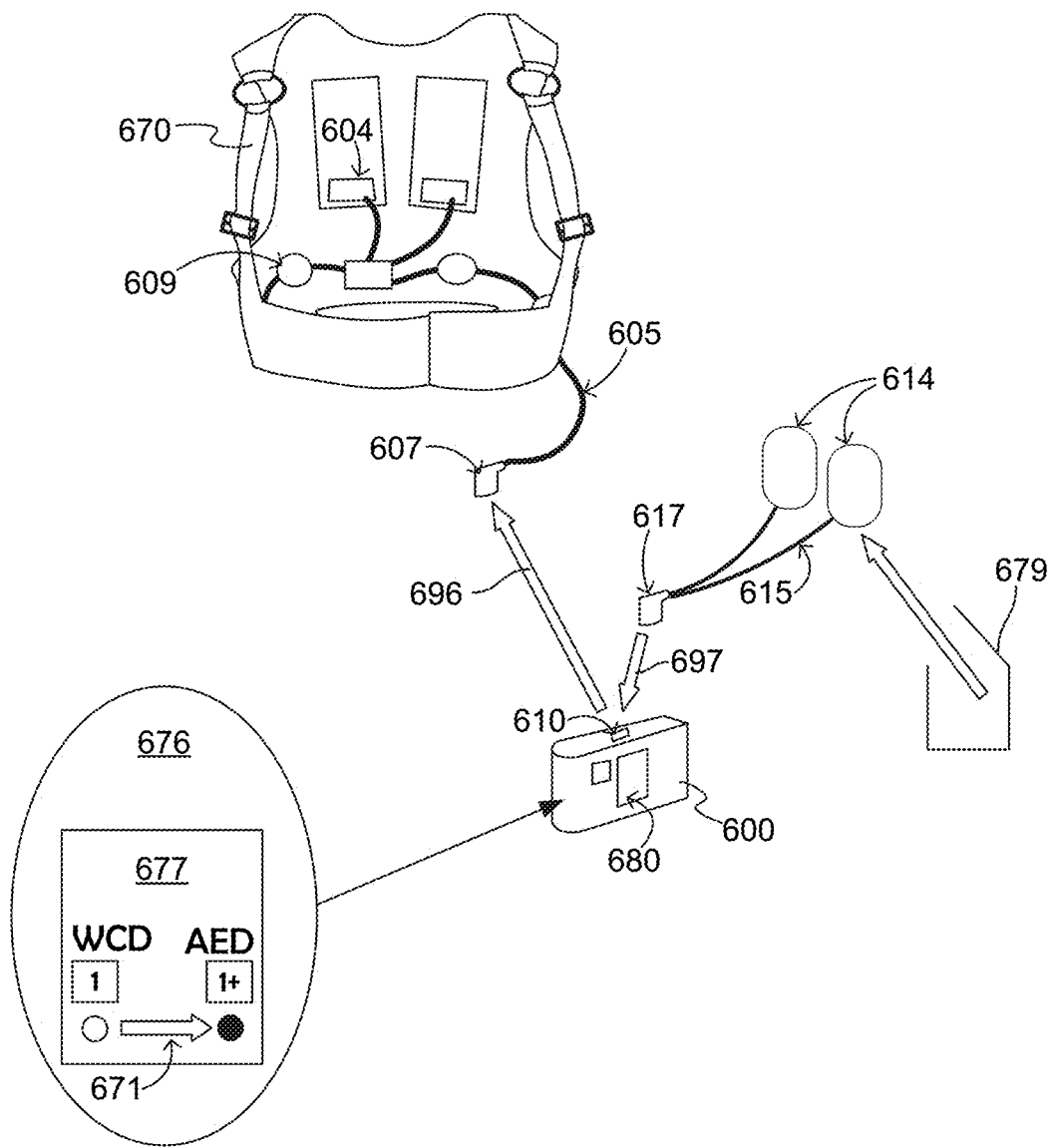
FIG. 6 is a diagram showing a sample embodiment of the WCD system of FIGS. 5A & 5B, in which the defibrillator uses a single socket for WCD electrodes and for AED electrodes.

FIG. 6 shows sample embodiments for the WCD system of FIGS. 5A & 5B, adapted from the example of FIG. 2. The WCD system has a support structure 670. Support structure 670 maintains on the patient's body ECG electrodes 609 and posterior electrode pads 604. These electrodes have a set of joined leads 605 that terminate in a single plug 607. Of course, plug 607 can have multiple pins for the different leads, etc.

The WCD system further includes a defibrillator 600. In this sample embodiment, a user interface 680 is on defibrillator 600, and is implemented via a touchscreen. Defibrillator 600 has a single defibrillation socket 610 on its housing. Defibrillation socket 610 can be electrically coupled with the energy storage module inside the housing.

For transitioning from the regular scenario of FIG. 5A to the emergency scenario of FIG. 5B, plug 607 is unplugged from defibrillation socket 610 according to an arrow 696, if it had not been so unplugged before. In addition, an AED electrode package 679 is opened to retrieve a pair of AED electrodes with pads 614 and leads 615 that terminate in a single plug 617. Plug 617 can be plugged into socket 610 according to arrow 697.

In conjunction with these preparations, or before them, defibrillator 600 may transition from a WCD mode to an AED mode. According to a comment 676, indicator 677 shows this transition with an arrow 671. Defibrillator 600 is thus ready for use as in FIG. 5B.

Figure 7:
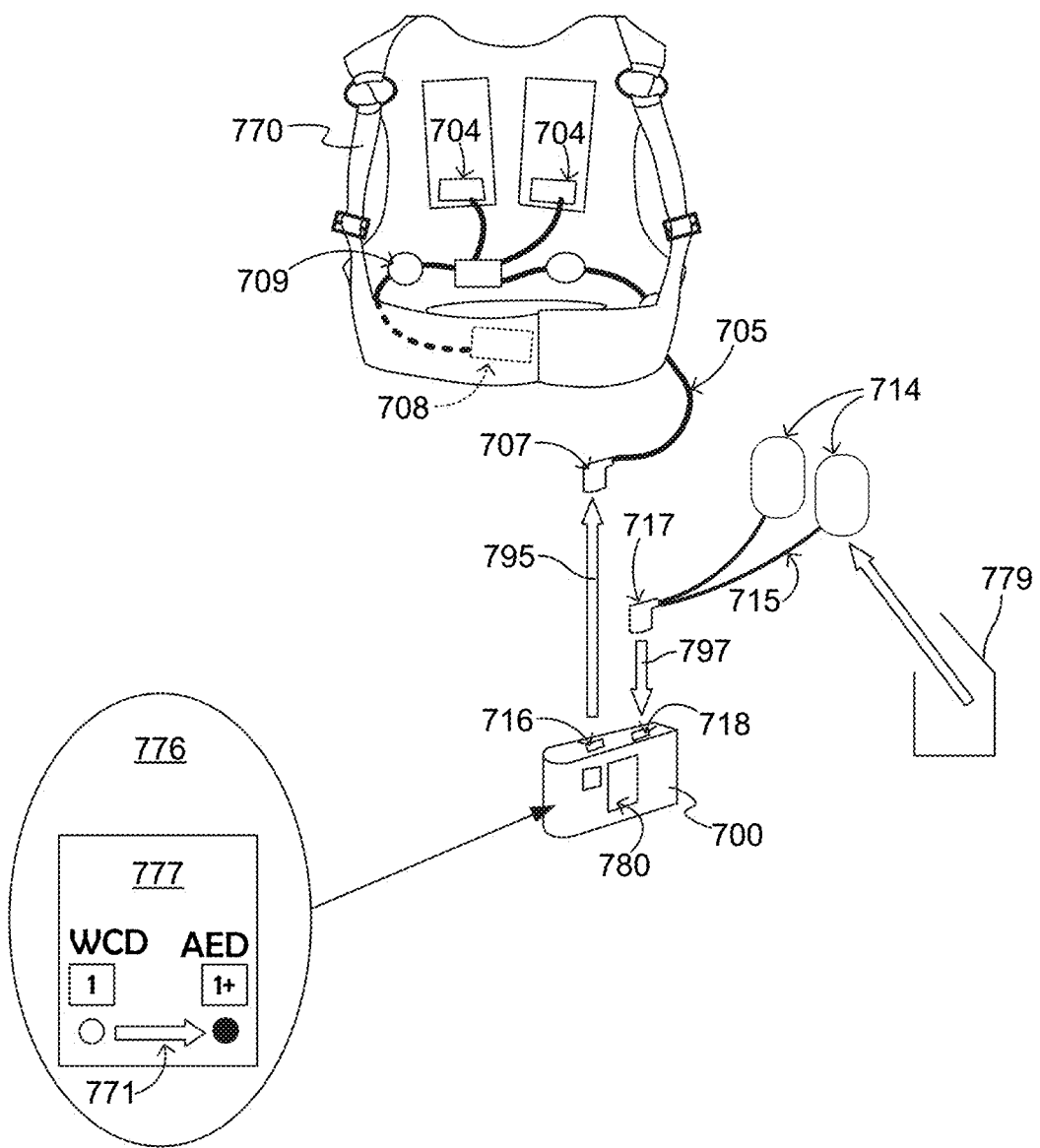
FIG. 7 is a diagram showing an additional sample embodiment of the WCD system of FIGS. 5A & 5B, in which the defibrillator uses different sockets for WCD electrodes and for AED electrodes.

FIG. 7 shows additional sample embodiments for the WCD system of FIGS. 5A & 5B, which are also adapted from the example of FIG. 2. The WCD system has a support structure 770. Support structure 770 maintains on the patient's body ECG electrodes 709 and a set of defibrillation electrodes that include posterior pads 704 and an anterior pad 708. All these electrodes have a set of joined leads 705 that terminate in a single plug 707. Pads 704, 708 can also be called first pads, and can be configured to be coupled to support structure 770, so that they are maintained on a body of the patient when the support structure is worn by the patient.

The WCD system further includes a defibrillator 700 with a user interface 780 that is implemented via a touchscreen. Defibrillator 700 has a first defibrillation socket 716 and a second defibrillation socket 718 on its housing. Defibrillation sockets 716 and 718 can be electrically coupled with the energy storage module inside the housing. In such cases, for additional safety, the design of the electrical circuit within the housing would be advantageously such that the defibrillation charge reaches only a socket in which a plug has been inserted. In addition, or alternatively, inserting a plug may mechanically open a small internal door for the electrical contacts of the socket, while otherwise the door remains closed. Plug 707 can be configured to be coupled into first defibrillation socket 716, for example by plugging, while the patient is wearing the support structure.

For transitioning from the regular scenario of FIG. 5A to the emergency scenario of FIG. 5B, plug 707 is optionally and preferably unplugged from defibrillation socket 716 according to an arrow 796, if it had not been so unplugged before. In addition, an AED electrode package 779 is opened to retrieve a second set of electrodes with second pads 714 and leads 715 that terminate in a single plug 717. Second pads 714 may include adhesive material, and can be configured to be maintained on the patient's body via the adhesive material as is known for AED electrodes. Plug 717 can be configured to be coupled into second defibrillation socket 718, for example by plugging according to arrow 797.

In conjunction with these preparations, or before them, defibrillator 700 may transition from a WCD mode to an AED mode. According to a comment 776, indicator 777 shows this transition with an arrow 771. Defibrillator 700 is thus ready for use as in FIG. 5B.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

More methods are now described.

Figure 8:
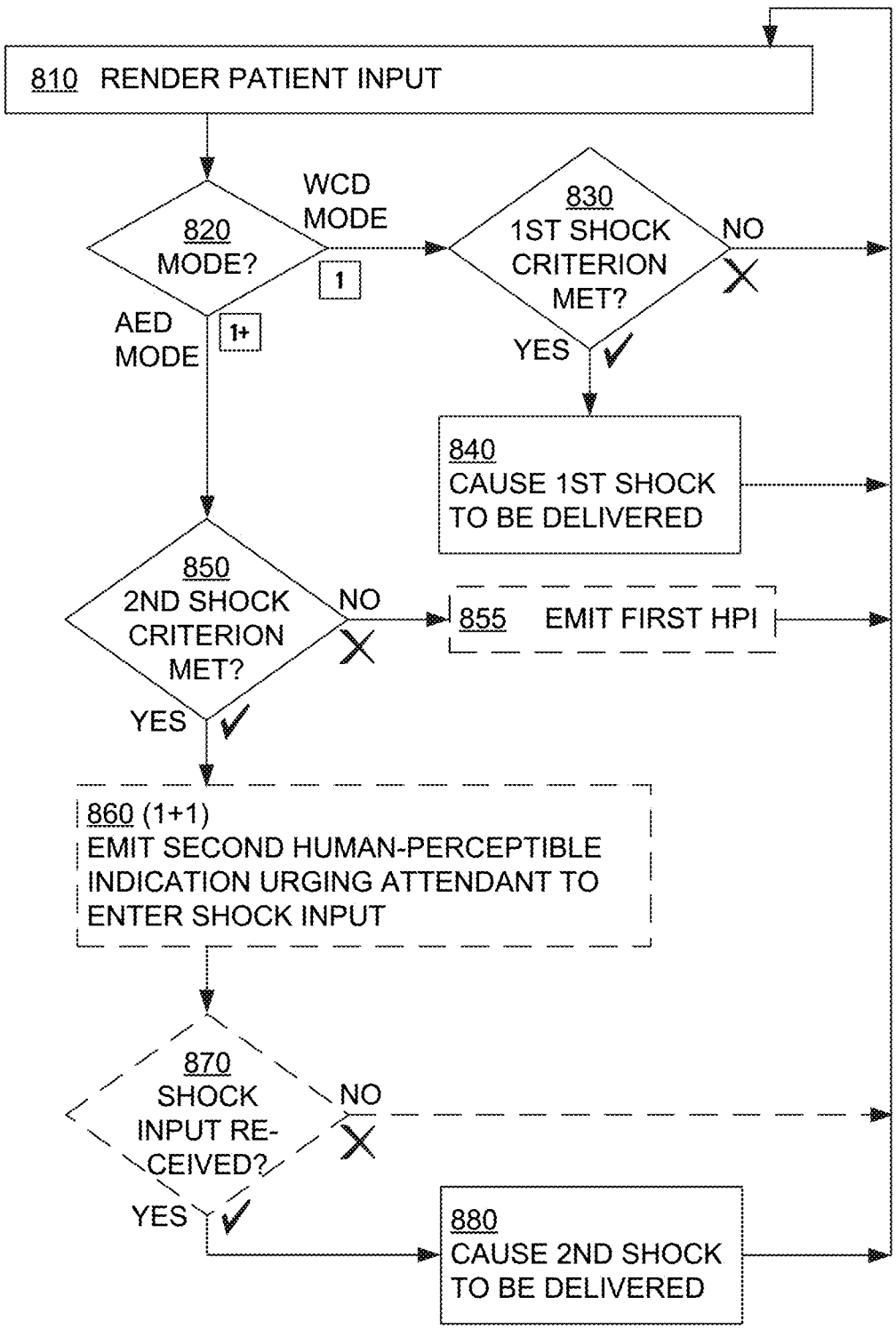
FIG. 8 is a flowchart for illustrating sample methods according to embodiments.

FIG. 8 shows a flowchart 800 for describing methods according to embodiments. According to an operation 810, a patient input may be rendered. Rendering may be performed responsive to the sensed parameter of the patient. According to another operation 820, it may be inquired what mode a processor or defibrillator is operating in.

If the answer at operation 820 is "WCD MODE" then, according to another operation 830 it may be determined whether or not a first shock criterion is met. This determination maybe performed from the patient input rendered at operation 810. If the answer is "NO", then execution may return to another operation, such as operation 810. If the answer is "YES" then, according to another operation 840, a first shock can be caused to be delivered to the patient when the patient is wearing the support structure. Operation 840 may be performed by causing at least some of the electrical charge stored in the energy storage module to be discharged through the patient. In some embodiments, discharge of operation 840 takes place via a first defibrillation electrode but not via a second defibrillation electrode, as described above. In embodiments such as those of FIG. 7, discharge of operation 840 may take place via first defibrillation socket 716, but not via second defibrillation socket 718.

If the answer at operation 820 is "AED MODE" then, according to another operation 850 it may be determined whether or not a second shock criterion is met. For example, a processor can be further configured to determine whether or not the second shock criterion is met. This determination maybe performed from the patient input rendered at operation 810. In some embodiments, the second shock criterion is the same as the first shock criterion.

If the answer at operation 850 is "NO", then execution may return to another operation, such as operation 810. Before doing that, according to another optional operation 855, a first human-perceptible indication ("HPI") may be emitted from an output device of the user interface, to the effect that a shock will be not administered at this time. This first HPI may be useful to an observer, such as an attendant or even the patient himself at that time.

If the answer at operation 850 is "YES" then, according to another operation 880, a second shock can be caused to be delivered to the patient. Operation 880 may be performed by causing at least some of the electrical charge stored in the energy storage module to be discharged through the patient. In some embodiments, the discharge of operation 880 takes place via a second defibrillation electrode but not via a first defibrillation electrode, as described above. Such would happen directly, for example, if the AED mode were the fully automatic mode ("1+0"). In embodiments such as those of FIG. 7, discharge of operation 880 may take place via second defibrillation socket 718, but not via first defibrillation socket 716.

In some embodiments, where the AED mode is the semi-automatic mode ("1+1"), if the answer at operation 850 is "YES" then, according to another, optional operation 860, a second human-perceptible indication may be emitted by the output device. This second HPI may urge attendant 83 to enter a shock input in the user interface, for example by pressing a button, and so on. This operation 860 may be performed responsive to the second shock criterion being met, as determined at operation 850. Then, according to another operation 870, it may be inquired whether or not a shock input has been received. Such a shock input may be received by the shock input device, if entered by attendant 83.

If the answer at operation 870 is "YES" then, execution proceeds to operation 880 as per the above. If, however, the answer at operation 870 is "NO", then execution may return to another operation, such as operation 810.

From operation 820 in the above, it can be appreciated different modes can make the defibrillator operates differently. For example, when the defibrillator or the processor is in the AED mode, it can be configured to cause the second human-perceptible indication of operation 860 to be emitted. However, when the defibrillator or the processor is in the WCD mode, it can be configured to not cause the second human-perceptible indication to be emitted, even if the second shock criterion is met.

Figure 9:
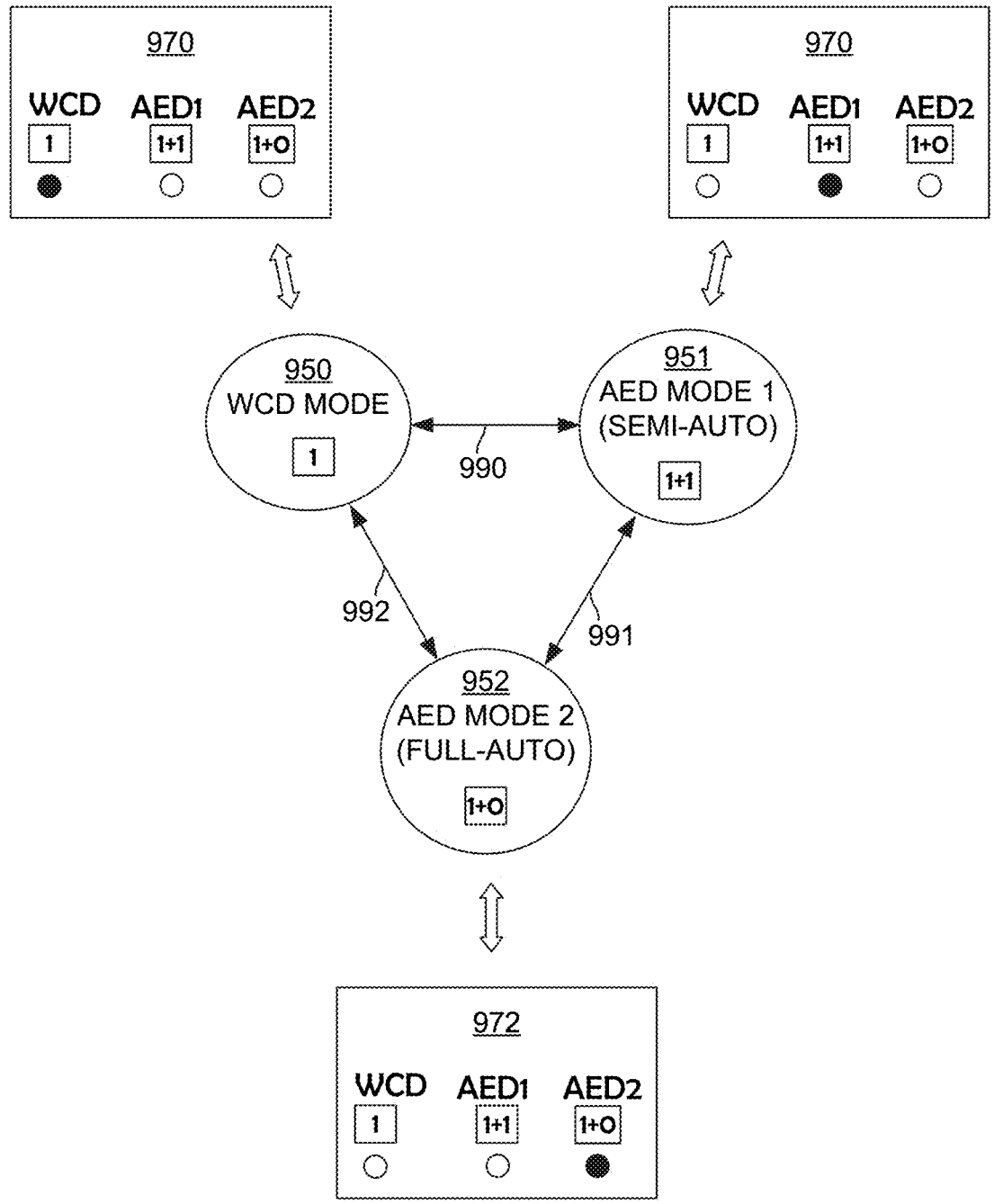
FIG. 9 is a diagram that shows possible modes of a WCD system according to embodiments.

FIG. 9 is a diagram that shows possible modes 950, 951, 952 of a WCD system according to embodiments. Mode 950 is a WCD mode, as indicated by indicator 970. Mode 951 is a first AED mode, and can be characterized by indicator 971. Mode 951 is a semi-automatic mode where the defibrillator does not deliver a shock unless the attendant enters a shock input. Mode 952 is a second AED mode, as indicated by indicator 972. Mode 952 is a fully-automatic mode, where the defibrillator delivers a shock when the second criterion of operation 850 is met, without needing the attendant to enter a shock input.

A defibrillator and/or its processor according to embodiments can therefore alternate among these modes. For example, the processor can be configured to alternate between being in WCD mode 950 and being in an AED mode 951 distinct from WCD mode 950, in which the processor behaves differently in each of these modes, as per the above.

It will be observed that, in the diagram of FIG. 9, there are two AED modes in addition to the WCD mode 950. Looking back at FIG. 8, more decision boxes can be inserted as to what type of AED mode the processor is in. And, looking further back at FIGS. 3B and 5B, each of defibrillators 300, 500 could be operating in either mode 951 or mode 952.

Returning to FIG. 9, it is not necessary for a WCD system according to embodiments to have the two AED modes of FIG. 9. For example, a WCD system may be provided with only one AED mode, for instance only one of modes 951, 952. In some embodiments a WCD system is provided with two AED modes, but one of them is disabled at the time of setup.

As mentioned above, in some embodiments portions of the user interface is located on the housing of the defibrillator. In some of these embodiments, an output device of the user interface can be located on the housing. Examples are now described.

Figure 10:
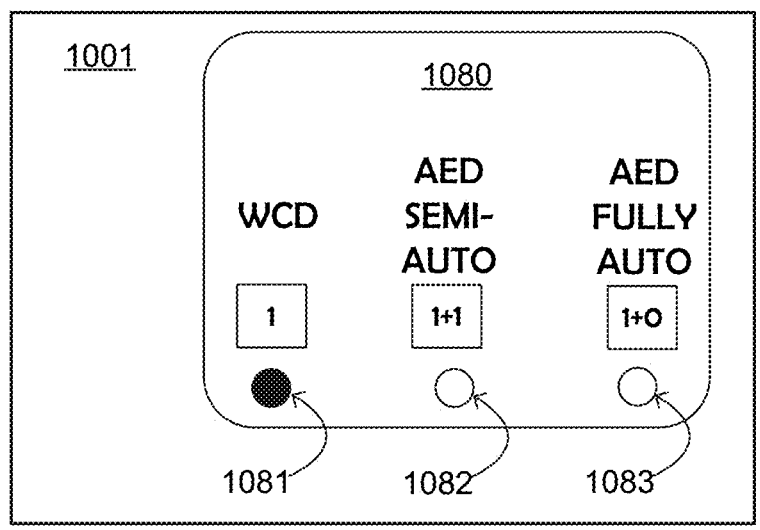
FIG. 10 is a diagram of a sample user interface that indicates which mode has been selected by a defibrillator of a WCD system that is made according to embodiments.

FIG. 10 is a diagram of a sample user interface that indicates which mode has been selected in a WCD system that is made according to embodiments. The user interface includes a screen 1080 that is on a housing 1001 of the defibrillator. Three indicators 1081, 1082, 1083 are possible. Of those, indicator 1081 is lit, indicating that the WCD mode is the current one.

FIG. 11 is a diagram of a sample user interface 1180, provided on a housing 1101 of a defibrillator. User interface 1180 has a first section 1181 for a WCD mode, which can be a screen, and is not indicated by illumination per the indicator scheme of FIG. 10.

User interface 1180 also has a second section 1182 for an AED mode. Second section 1182, which can be a touchscreen, has three subsections that can be defined on the screen as buttons, etc. Section 1184, when indicated, writes: "STAND CLEAR—ANALYZING NOW". Section 1185, when indicated, writes: "NO SHOCK ADVISED—PERFORM CPR". CPR stands for cardiopulmonary resuscitation, and involves attendant 83 administering chest compressions and rescue breaths to the patient. In conjunction, user interface 1180 may output CPR metronome sounds, like "Toc . . . Toc . . . Toc". Incidentally, voice prompts may be different in AED mode than the WCD mode, as they are directed toward exclusively the anticipated rescuer, namely attendant 83. On the other hand, WCD voice prompts are mostly directed toward patient 82, although a bystander prompt to stand clear can be given before a shock. In addition, section 1186, when indicated, writes: "SHOCK ADVISED—PUSH THIS BUTTON TO SHOCK". As such, section 1186 includes the shock input device of the user interface. In other embodiments, the shock input device could be part of the electrode wiring harness of the WCD system.

Somewhat similarly, FIG. 12 is a diagram of a sample user interface 1280, provided on a housing 1201 of a defibrillator. User interface 1280 has a first section 1281 for a WCD mode, which can be a screen, and is not indicated by illumination per the indicator scheme of FIG. 10.

User interface 1280 further has a second section 1282 for an AED mode. Second section 1282, which can be a screen, has three subsections that can be defined on the screen as buttons, etc. Section 1284, when indicated, writes: "STAND CLEAR—ANALYZING NOW". Section 1285, when indicated, writes: "NO SHOCK ADVISED—PERFORM CPR". Section 1286, when indicated, writes: "SHOCK ADVISED—STAND CLEAR!".

It should be observed that the user interfaces of FIGS. 10, 11, 12 do not indicate how the current mode has been selected. More particularly, returning to FIG. 9 it can be appreciated that a defibrillator and/or its processor according to embodiments may be further configured to transition among the modes, for example according to arrows 990, 991, 992. As such, the processor may transition from being in one of AED mode 951 and WCD mode 950 to being in the other one of AED mode 951 and WCD mode 950. The same can of course apply between any pair of modes, such as the modes of FIG. 9.

In some embodiments, such a mode transition is performed responsive to a transition condition being met. There can be a number of such transition conditions according to embodiments. These may be divided into two main categories, namely a) mode selected by a human and b) mode selected by the system processor itself. In embodiments, both types of mode transition conditions may exist, also with default prioritization in case of conflicts, etc.

In some embodiments, the user interface further includes a mode selection input device, which is configured to receive a mode selection input entered by the attendant. In such embodiments, the transition condition is that the mode selection input is received by the mode selection input device. An example is now described.

Figure 13:
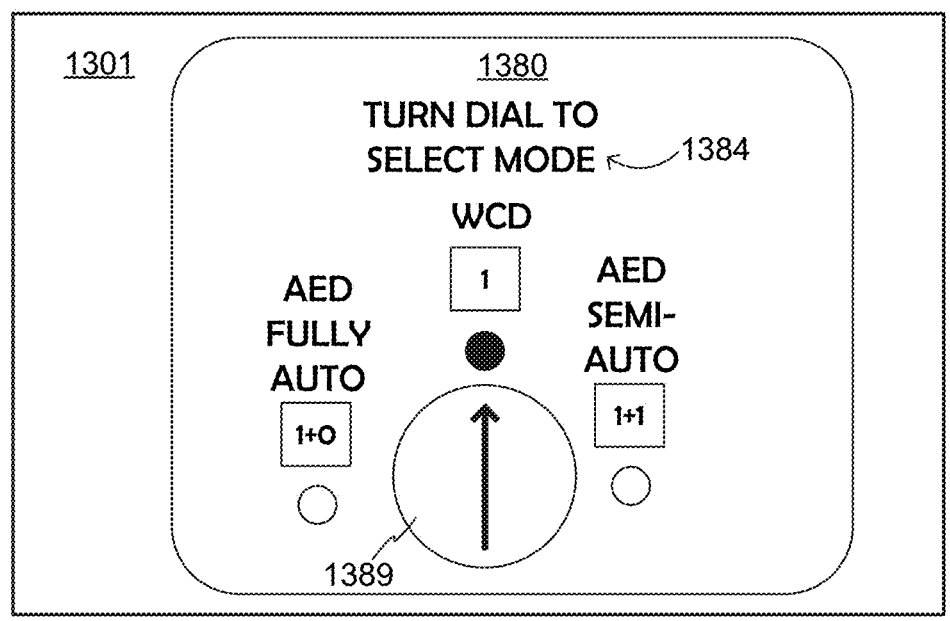
FIG. 13 is a diagram of a sample user interface that enables the user to select a mode of operation, in a WCD system made according to embodiments.

FIG. 13 is a diagram of a sample user interface in a WCD system that is made according to embodiments that both permits selecting a mode, and further indicates which mode has been selected. The user interface includes a panel 1380 that is on a housing 1301 of the defibrillator. An inscription 1384 on the panel includes the instruction: "TURN DIAL TO SELECT MODE". A dial 1389 permits selecting one of three modes. As seen in FIG. 13, the WCD mode is selected. Other embodiments can be with a touchscreen and not a physical dial, or with repeatedly pushing a button to step through possible choices until the desired one appears, and so on.

Other mode transition conditions can be met by the system itself, and may control transitions automatically, regardless of inputs by attendant 83 or even patient 82. For example, a transition condition can be that a preset time duration has passed during which the processor has been in one of AED mode 951 and WCD mode 950, and therefore it is time to switch to a default. A default can be WCD mode 950.

For other embodiments of mode transition conditions, the processor may be configured to detect certain electrical connections of the electrodes, from what is plugged in to which socket, what signal is sensed, and so on. In such embodiments, the transition condition can be that the certain electrical connection is detected. The detected certain electrical connection can be: i) an impedance that suggests disconnection when infinite, suggests connection when having patient-like values between 50 Ohm and 300 Ohm, suggests activity by attendant 83 if it changes suddenly, ii) an ECG signal whose presence suggests connection and absence suggests disconnection, suggests conditions of connection depending on whether or not it has noise (adhered to electrode will have less noise than conductive surface electrodes), iii) indicates electrode function (WCD or AED) from electrode identification signals such as RFID (Radio Frequency Identification) signals, etc.

In some embodiments, defibrillators are provided with extra-long wire leads. Such a defibrillator can be either an AED or the defibrillator component of a WCD system. In such embodiments, the patient may set down the housing of the defibrillator without having to carry it, and still have limited mobility. This may prove useful when eating, watching TV, or sleeping. Examples are now described.

FIG. 14 is a diagram of a defibrillator 1400, which has a socket 1410 in its housing. A set of defibrillation electrodes includes a plug 1417, which can be plugged into and out of socket 1410. The defibrillation electrodes also include two electrode pads 1404, 1414, between which a shock 1411 can be delivered. The defibrillation electrodes also include two flexible wire leads 1415, 1416. Wire lead 1415 has a first end 1431 attached to electrode pad 1404, and a second end 1432 attached to plug 1417. Wire lead 1415 has a length of at least 5 ft (152 cm) between its first end 1431 and its second end 1432. The other wire lead 1416 can be sized similarly to wire lead 1415. In some embodiments, the lengths are even longer, for example at least 6 ft (183 cm), at least 7 ft (213 cm), at least 8 ft (244 cm), 9 feet (ft) and so on.

In the example of FIG. 14, electrode pad 1404 includes an adhesive material 1423. In this example, a liner 1408 is also provided, which can be peeled from pad 1404 by its edge 1409. Alternately, electrodes with no adhesive material could be used, for example by a WCD system.

As mentioned above, defibrillator 1400 can be either an AED or the defibrillator component of a WCD system. For the latter, a defibrillator system would further include a support structure configured to be worn by the patient; the support structure can be configured to maintain pads 1404, 1414 on a body of the patient when the support structure is worn by the patient.

It should be noted that a support structure for the example of FIG. 14 need not be a full support structure, in that it need not carry also defibrillator 1400. Examples are described below.

In embodiments, an environmentally-protected accessory plugs into socket 1410. The accessory can be designed to support harsher environments than the standard WCD system (e.g., a shower), and provide adhesive defibrillation pads capable of staying attached to the patient in that harsh environment. Patient 82 may self-apply such defibrillation pads and connect the accessory to defibrillator 1400, activating a suitable mode.

Different techniques to protect the defibrillator from the harsh environment may be employed to allow patient 82 to enter the harsh environment, including: a) extra-long wire leads as described above, b) a water-tight "shower bag" for the electronics module, and c) an electronics module and connector that supports the harsh environment and can be used directly without protecting it. An example is are now described.

FIG. 15 is a diagram of a patient 1582. Patient 1582 is wearing a sample WCD system that has a defibrillator 1500, and uses a cable 1505 that can be extra-long according to embodiments, for example with length as described above. Patient 1582 is wearing only an upper vest 1571 of a support structure. Defibrillator 1500 may operate in a prophylactic mode that is a fully-automatic AED mode. For example, it could be receiving an ECG signal from the defibrillation electrodes, and shock through the if need be.

The extra-long cable 1505 includes the wire leads, and permits patient 1582 a modicum of mobility away from defibrillator 1500. For example, patient 1582 could be eating or watching TV. Patient 1582 may even take a shower, while leaving defibrillator 1500 outside the path of water, and elevated as water may drip from patient 1582 along cable 1505 towards defibrillator 1500.

Patient 1582 can be considered shown upright in FIG. 15. Or, patient 1582 could be on a sleeping surface 1502, such as a bed, shown only partly. Patient 1582 could be bedridden, or sleeping only for the night. The extra-long cable 1505 permits patient 1582 to set defibrillator 1500 on a base surface 1503, such as a table 1503, shown only partly.

Figure 16:
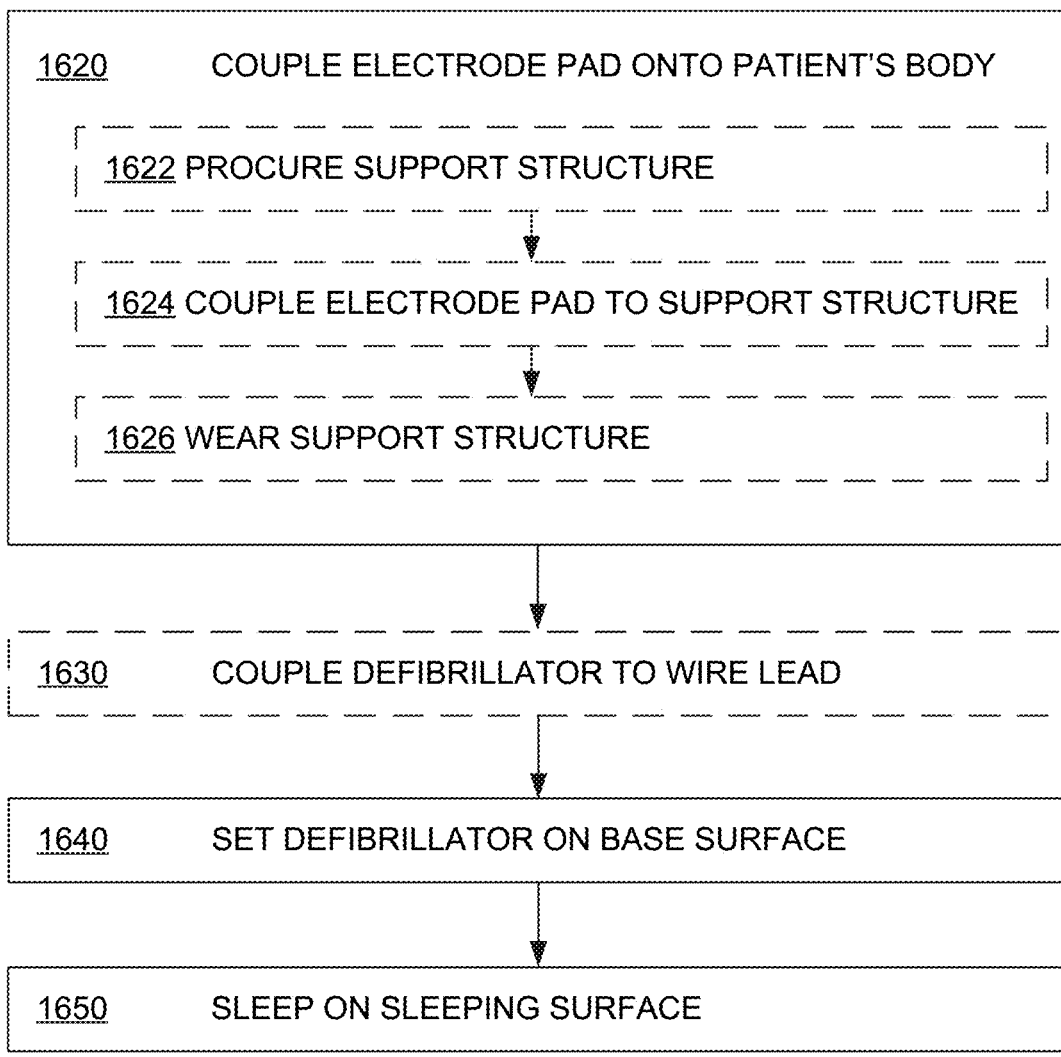
FIG. 16 is a flowchart for illustrating sample methods according to embodiments.

A related method is now described. FIG. 16 shows a flowchart 1600 for describing methods according to embodiments.

According to an operation 1620, an electrode pad is coupled onto a body of the patient. The electrode pad can be coupled to the wire lead. Operation 1620 may be performed in a number of ways. In some embodiments, the electrode pad includes an adhesive material, and the electrode pad is coupled onto the body of the patient using the adhesive material. In other embodiments, operation 1620 may be performed by operations 1622, 1624, 1626. According to operation 1622, a support structure may be procured, such as vest 1571. According to operation 1624, the electrode pad may be coupled to the support structure. According to operation 1626, the support structure may be worn so the support structure maintains the electrode pad onto the patient's body.

According to an optional operation 1630, a defibrillator can be coupled to a wire lead, which can be extra-long as per the above. This operation is optional because the defibrillator may be provided already coupled to the wire lead.

According to another, optional operation 1640, the defibrillator may be set on a base surface 1503.

According to another operation 1650, the patient may sleep on a sleeping surface, such as a bed 1502, which is different from the sleeping surface. Operation 1650 may take place when the electrode pad is thus coupled, and the defibrillator is coupled to the second end of the wire lead.

Figure 17:
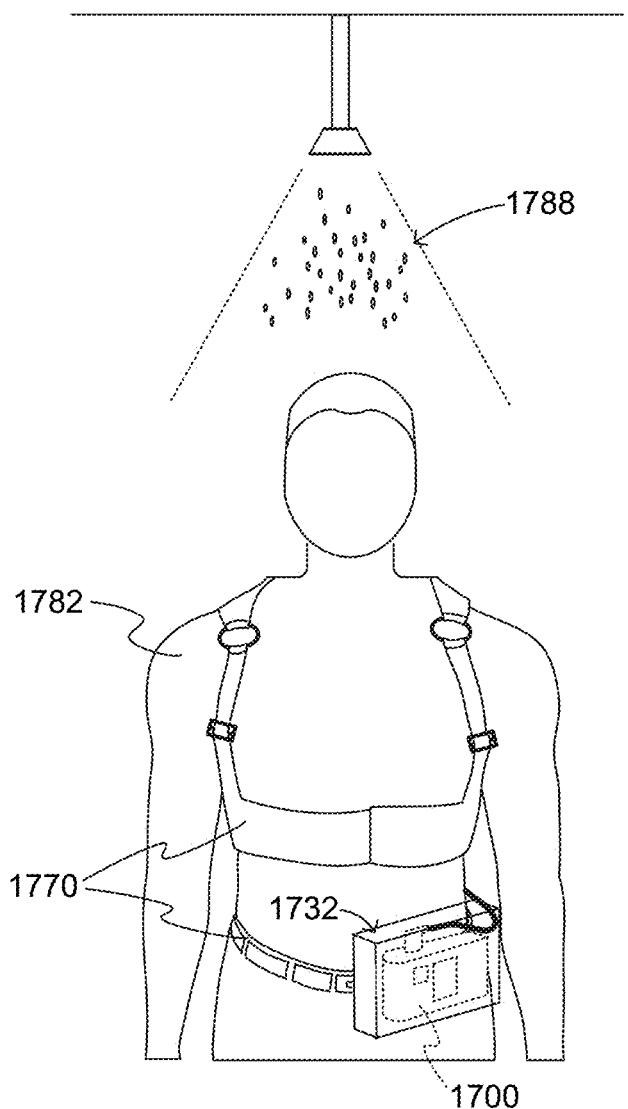
FIG. 17 is a diagram of a WCD system that uses a watertight cover for its defibrillator according to embodiments.

FIG. 17 is a diagram of a waterproof WCD system that uses a watertight cover according to embodiments. A patient 1782 is taking a shower by sprayed water 1788. Patient 1782 wears a support structure 1770, which supports on him a defibrillator 1700.

A watertight cover 1732 surrounds defibrillator 1700. Watertight cover 1732 can be made from materials that are waterproof, such as plastic. In some embodiments, cover 1732 includes a plastic bag, with openings for the wires that emanate from it and its means of attachment to the support structure. Watertight cover 1732 can be transparent at least in places where it is desired to look at the user interface of defibrillator 1700.

Figure 18:
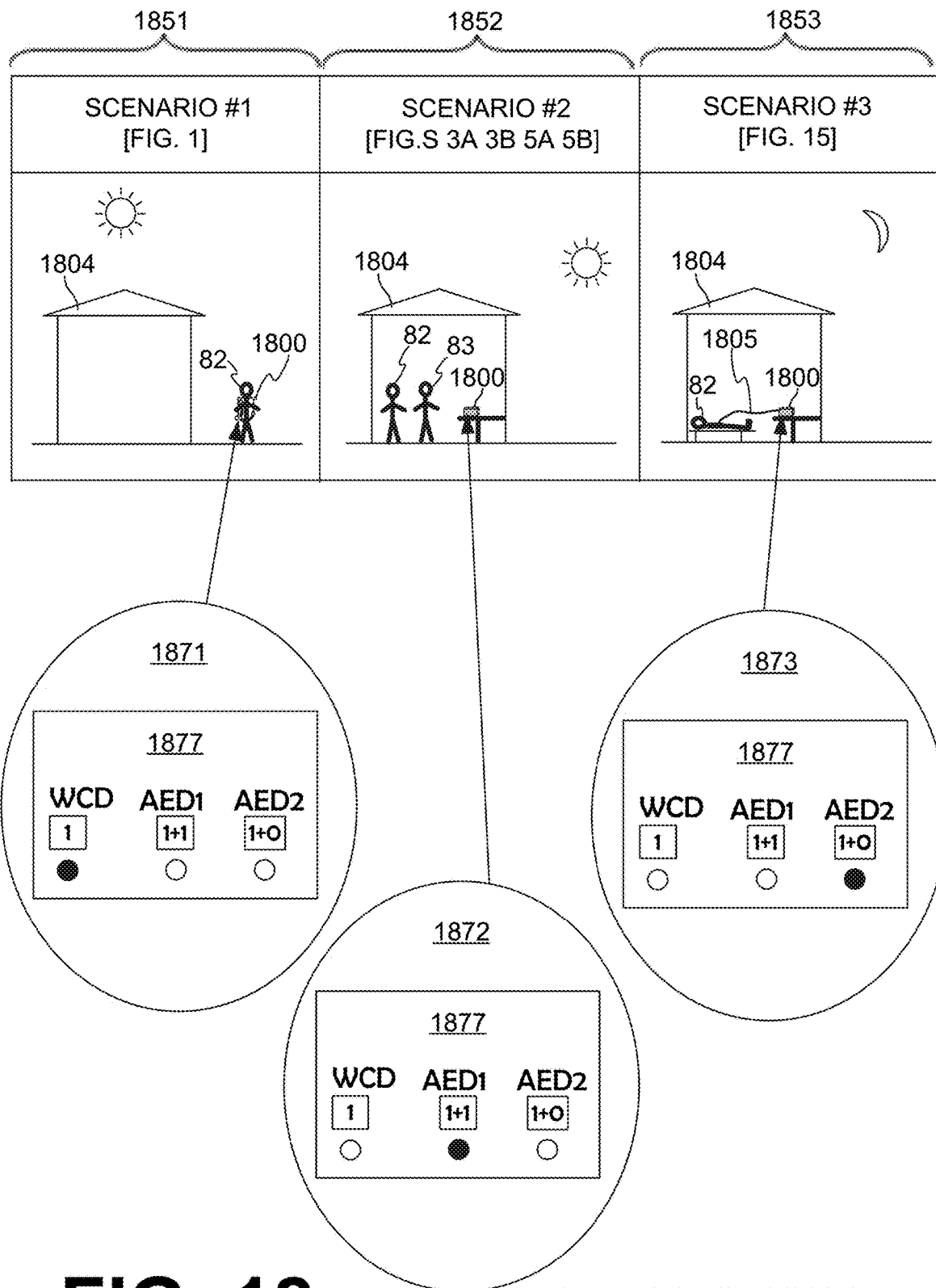
FIG. 18 is a table that depicts graphically different sample scenarios from a daily routine of a patient who is protected by a sample WCD system that also has AED modes according to embodiments.

FIG. 18 is a table that depicts graphically three different sample scenarios 1851, 1852, 1853 from a daily routine of patient 82 who lives in a home 1804. Patient 82 has a WCD system according to embodiments, which includes a defibrillator 1800. An indicator 1877 indicates the current mode of defibrillator 1800 during each scenario.

Scenario #1 1851 takes place during the day, when patient 82 may be outside their home 1804. Patient 82 is wearing defibrillator 1800 on their body, for example as seen in FIG. 1. According to a comment 1871, indicator 1877 indicates that, during that time, defibrillator 1800 is in the WCD "1" mode.

Scenario #2 1852 takes place during the evening, when patient 82 may be in their home 1804, and socializing, dining, watching TV, etc. Under the oversight of an attendant 83, patient 82 is not wearing defibrillator 1800 on their body, and possibly not any component of the WCD system, for example as seen in FIGS. 3A and 5A. In the event of a health emergency, attendant 83 can use defibrillator 1800 in an AED mode, for example as seen in FIGS. 3B and 5B. In the example of FIG. 18, according to a comment 1872, indicator 1877 indicates that defibrillator 1800 during that time is in an AED "1+1" mode, where attendant 83 is needed to press the button for delivering a defibrillation shock.

Scenario #3 1853 takes place during the night, when patient 82 is sleeping in their home 1804. Patient 82 is wearing the electrodes, but not defibrillator 1800, for example as seen in FIG. 15. Defibrillator 1800 may have been set on a table, and be connected to the electrodes via extra-long cable 1805. According to a comment 1873, indicator 1877 indicates that defibrillator 1800 during that time is in an AED "1+0" mode, where no attendant 83 is needed to press the button for delivering a defibrillation shock.

Figure 19:
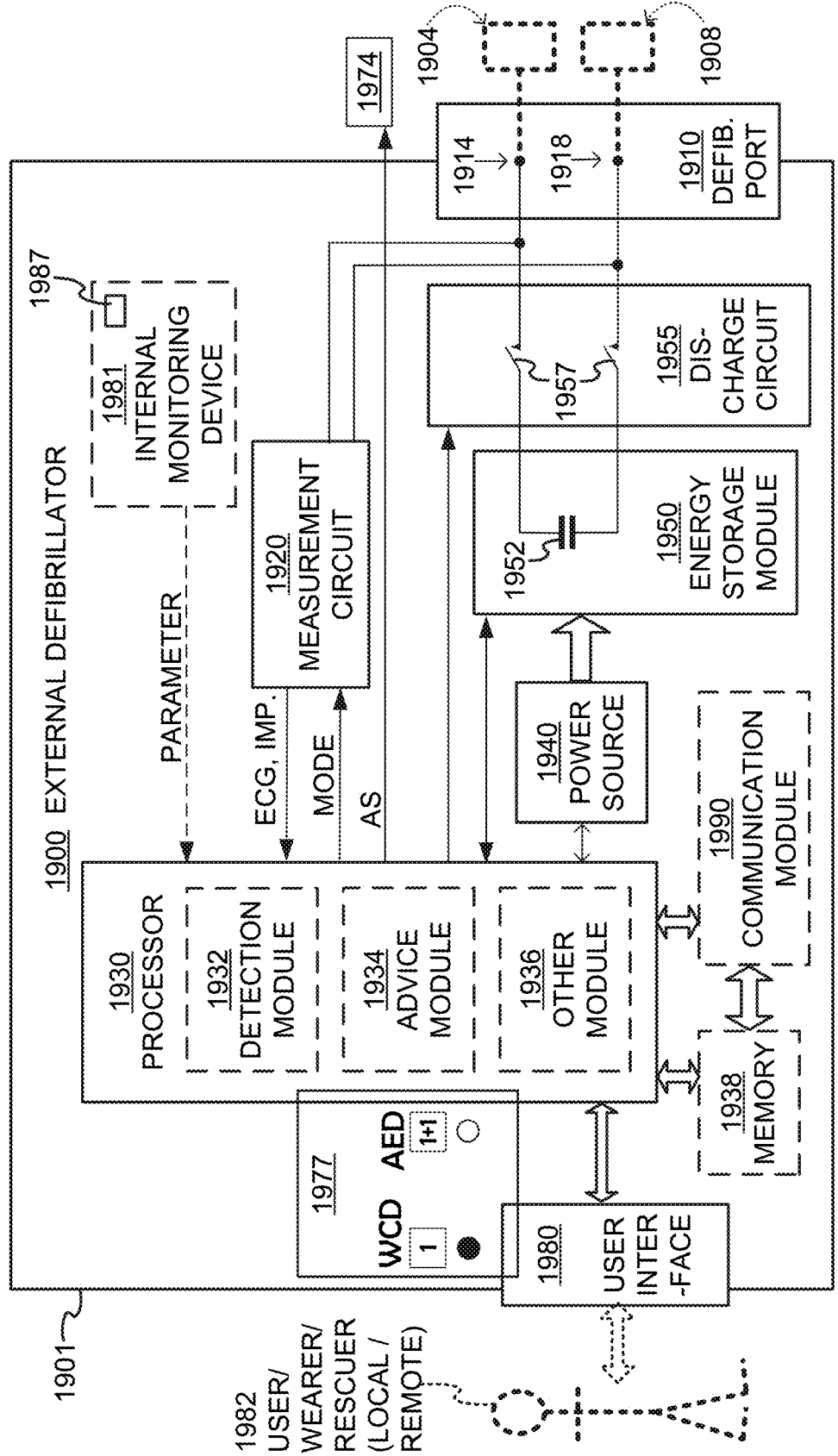
FIG. 19 is a diagram showing sample components of an external defibrillator, which is made according to an embodiment that uses two electrodes for sensing the patient's ECG and for defibrillating the patient.

FIG. 19 is a is a diagram showing sample components of an external defibrillator 1900, which is made according to an embodiment that uses exactly two electrodes for sensing the patient's ECG and for defibrillating the patient. It will be appreciated that such embodiments can transition from the WCD mode to the AED mode with less reconfiguration.

The sample components of defibrillator 1900 can be, for example, included in external defibrillator 100 of FIG. 1, or many other sample defibrillator embodiments shown and described in this document. The components shown in FIG. 19 can be provided in a housing 1901, which may also be referred to as casing 1901.

External defibrillator 1900 is intended for patient 82 who may be wearing it. Defibrillator 1900 may further include a user interface 1980 for a user 1982. User 1982 can be patient 82, also known as wearer 82. Or, user 1982, who is also known as rescuer 1982, can be attendant 83. Or, user 1982 might be a remotely located trained caregiver in communication with the WCD system.

User interface 1980 can be made in a number of ways. User interface 1980 may include output devices, which can be visual, audible or tactile, for communicating to a user by outputting images, sounds or vibrations. Images, sounds, vibrations, and anything that can be perceived by user 1982 can also be called human-perceptible indications (HPIs). There are many examples of output devices. For example, an output device can be a light, or a screen to display what is sensed, detected and/or measured, and provide visual feedback to rescuer 1982 for their resuscitation attempts, and so on. Another output device can be a speaker, which can be configured to issue voice prompts, beeps, loud alarm sounds and/or words to warn bystanders, etc.

User interface 1980 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock. Another input device is a shock input device, for example as seen in the pushbutton in section 1186. That pushbutton may be mechanical, implemented by a touchscreen, etc.

Defibrillator 1900 may include an internal monitoring device 1981. Device 1981 is called an "internal" device because it is incorporated within housing 1901. Monitoring device 1981 can sense or monitor patient parameters such as patient physiological parameters, system parameters and/or environmental parameters, all of which can be called patient data. In other words, internal monitoring device 1981 can be complementary or an alternative to outside monitoring device 180 of FIG. 1. Allocating which of the parameters are to be monitored by which of monitoring devices 180, 1981 can be done according to design considerations. Device 1981 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 1981 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 1982. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 1982 will know about a condition that is either not improving or deteriorating.

Patient state parameters include recorded aspects of patient 1982, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 1981. Such a motion detector can be made in many ways as is known in the art, for example by using an accelerometer. In this example, a motion detector 1987 is implemented within monitoring device 1981. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 1981 includes a GPS location sensor as per the above, and if it is presumed that the patient is wearing the WCD system.

Defibrillator 1900 typically includes a defibrillation port 1910, which can be a socket in housing 1901. Defibrillation port 1910 includes electrical nodes 1914, 1918. Leads of defibrillation electrodes 1904, 1908, such as leads 105 of FIG. 1, can be plugged into defibrillation port 1910, so as to make electrical contact with nodes 1914, 1918, respectively. It is also possible that defibrillation electrodes 1904, 1908 are connected continuously to defibrillation port 1910, instead. Either way, defibrillation port 1910 can be used for guiding, via electrodes, to the wearer the electrical charge that has been stored in an energy storage module 1950 that is described more fully later in this document. The electric charge will be the shock for defibrillation, pacing, and so on.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for defibrillation electrodes 1904, 1908.

The fluid may be initially stored in a fluid reservoir, not shown in FIG. 19. Such a fluid reservoir can be coupled to the support structure. In addition, a WCD system according to embodiments further includes a fluid deploying mechanism 1974. Fluid deploying mechanism 1974 can be configured to cause at least some of the fluid to be released from the reservoir, and be deployed near one or both of the patient locations to which electrodes 1904, 1908 are configured to be attached to the patient. In some embodiments, fluid deploying mechanism 1974 is activated prior to the electrical discharge responsive to receiving activation signal AS from a processor 1930, which is described more fully later in this document.

In some embodiments, defibrillator 1900 also includes a measurement circuit 1920, as one or more of its sensors or transducers. Measurement circuit 1920 senses one or more electrical physiological signals of the patient through nodes 1914, 1918, when defibrillation electrodes 1904, 1908 are attached to the patient. For the AED mode, some electrodes are used for both ECG and defibrillation function. The manner of sensing may be helped by a MODE signal from processor 1930, which indicates the prevalent mode. In these cases, the input reflects an ECG measurement. The patient parameter can be an ECG, which can be sensed as a voltage difference between electrodes 1904, 1908. Then the patient input can include values for the ECG signal. In addition, the patient parameter can be an impedance, which can be sensed between electrodes 1904, 1908 and/or between the connections of sensor port 1919 considered pairwise. Sensing the impedance can be useful for detecting, among other things, whether these electrodes 1904, 1908 are not making good electrical contact with the patient's body. These patient physiological signals may be sensed when available. Measurement circuit 1920 can then render or generate information about them as inputs, data, other signals, etc. More strictly speaking, the information rendered by measurement circuit 1920 is output from it, but this information can be called an input because it is received as an input by a subsequent device or functionality. Of course, measurement circuit 1920 can have isolation to prevent the defibrillation discharge from harming it. Such can be made as is known in the art of AEDs.

Defibrillator 1900 also includes a processor 1930. Processor 1930 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 1930 may include, or have access to, a non-transitory storage medium, such as memory 1938 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 1930 can be considered to have a number of modules. One such module can be a detection module 1932. Detection module 1932 can include a Ventricular Fibrillation (VF) detector. The patient's sensed ECG from measurement circuit 1920, which can be available as inputs, data that reflect values, or other signals, may be used by the VF detector to determine whether the patient is experiencing VF. Detecting VF is useful, because VF typically results in SCA. Detection module 1932 can also include a Ventricular Tachycardia (VT) detector, and so on. An ECG analysis algorithm would be similar between an AED and the WCD mode.

Another such module in processor 1930 can be an advice module 1934, which generates advice for what to do. The advice can be based on outputs of detection module 1932. There can be many types of advice according to embodiments. In some embodiments, the advice is a shock/no shock determination that processor 1930 can make, for example via advice module 1934. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

Processor 1930 can include additional modules, such as other module 1936, for other functions. In addition, if internal monitoring device 1981 is indeed provided, processor 1930 may receive its inputs, etc.

Indicator 1977 is shown conceptually as overlapping processor 1930, and indicates that, at this moment, the processor is in a WCD "1" mode, not in an AED mode. Moreover, indicator 1977 is shown as further overlapping user interface 1980, to signify that user 1982 may get to see what the current mode is, and even change it.

Defibrillator 1900 optionally further includes a memory 1938, which can work together with processor 1930. Memory 1938 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 1938 is thus a non-transitory storage medium. Memory 1938, if provided, can include programs for processor 1930, which processor 1930 may be able to read and execute. More particularly, the programs can include sets of instructions in the form of code, which processor 1930 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 1930, and can also include protocols and ways that decisions can be made by advice module 1934. In addition, memory 1938 can store prompts for user 1982, if this user is a local rescuer such as attendant 83, a bystander in Scenario #1 1851, etc. Moreover, memory 1938 can store data. This data can include patient data, system data and environmental data, for example as learned by internal monitoring device 1981 and outside monitoring device 180. The data can be stored in memory 1938 before it is transmitted out of defibrillator 1900, or be stored there after it is received by defibrillator 1900.

Defibrillator 1900 may also include a power source 1940. To enable portability of defibrillator 1900, power source 1940 typically includes a battery. Such a battery is typically implemented as a battery pack, which can be rechargeable or not. Sometimes a combination is used of rechargeable and non-rechargeable battery packs. Other embodiments of power source 1940 can include an AC power override, for where AC power will be available, an energy-storing capacitor, and so on. Appropriate components may be included to provide for charging or replacing power source 1940. In some embodiments, power source 1940 is controlled and/or monitored by processor 1930.

Defibrillator 1900 may additionally include an energy storage module 1950. Energy storage module 1950 can be coupled to the support structure of the WCD system, for example either directly or via the electrodes and their leads. Module 1950 is where some electrical energy can be stored temporarily in the form of an electrical charge, when preparing it for discharge to administer a shock. In embodiments, module 1950 can be charged from power source 1940 to the desired amount of energy, as controlled by processor 1930. In typical implementations, module 1950 includes a capacitor 1952, which can be a single capacitor or a system of capacitors, and so on. In some embodiments, energy storage module 1950 includes a device that exhibits high power density, such as an ultracapacitor. As described above, capacitor 1952 can store the energy in the form of an electrical charge, for delivering to the patient.

A decision to shock can be made responsive to the shock criterion being met, as per the above-mentioned determination. When the decision is to shock, processor 1930 can be configured to cause at least some or all of the electrical charge stored in module 1950 to be discharged through patient 82 while the support structure is worn by patient 82, so as to deliver a shock 111 to patient 82.

For causing the discharge, defibrillator 1900 moreover includes a discharge circuit 1955. When the decision is to shock, processor 1930 can be configured to control discharge circuit 1955 to discharge through the patient at least some of all of the electrical charge stored in energy storage module 1950. Discharging can be to nodes 1914, 1918, and from there to defibrillation electrodes 1904, 1908, so as to cause a shock to be delivered to the patient. Circuit 1955 can include one or more switches 1957. Switches 1957 can be made in a number of ways, such as by an H-bridge, and so on. Circuit 1955 could also be controlled via user interface 1980.

A time waveform of the discharge may be controlled by thus controlling discharge circuit 1955. The amount of energy of the discharge can be controlled by how much energy storage module has been charged, and also by how long discharge circuit 1955 is controlled to remain open.

Defibrillator 1900 can optionally include a communication module 1990, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 1990 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 1990 may also include such interconnected sub-components as may be deemed necessary by a person skilled in the art, for example an antenna, portions of a processor, supporting electronics, outlet for a telephone or a network cable, etc.

Defibrillator 1900 can optionally include other components.

In some embodiments, the defibrillator collects ECG data from electrodes other than the defibrillation electrodes. For example, the sensor may include an electrode additional to what is being described, which performs such ECG measurements. The additional electrode can be complementary to the first, an ECG-only electrode, etc. An example is now described.

Figure 20:
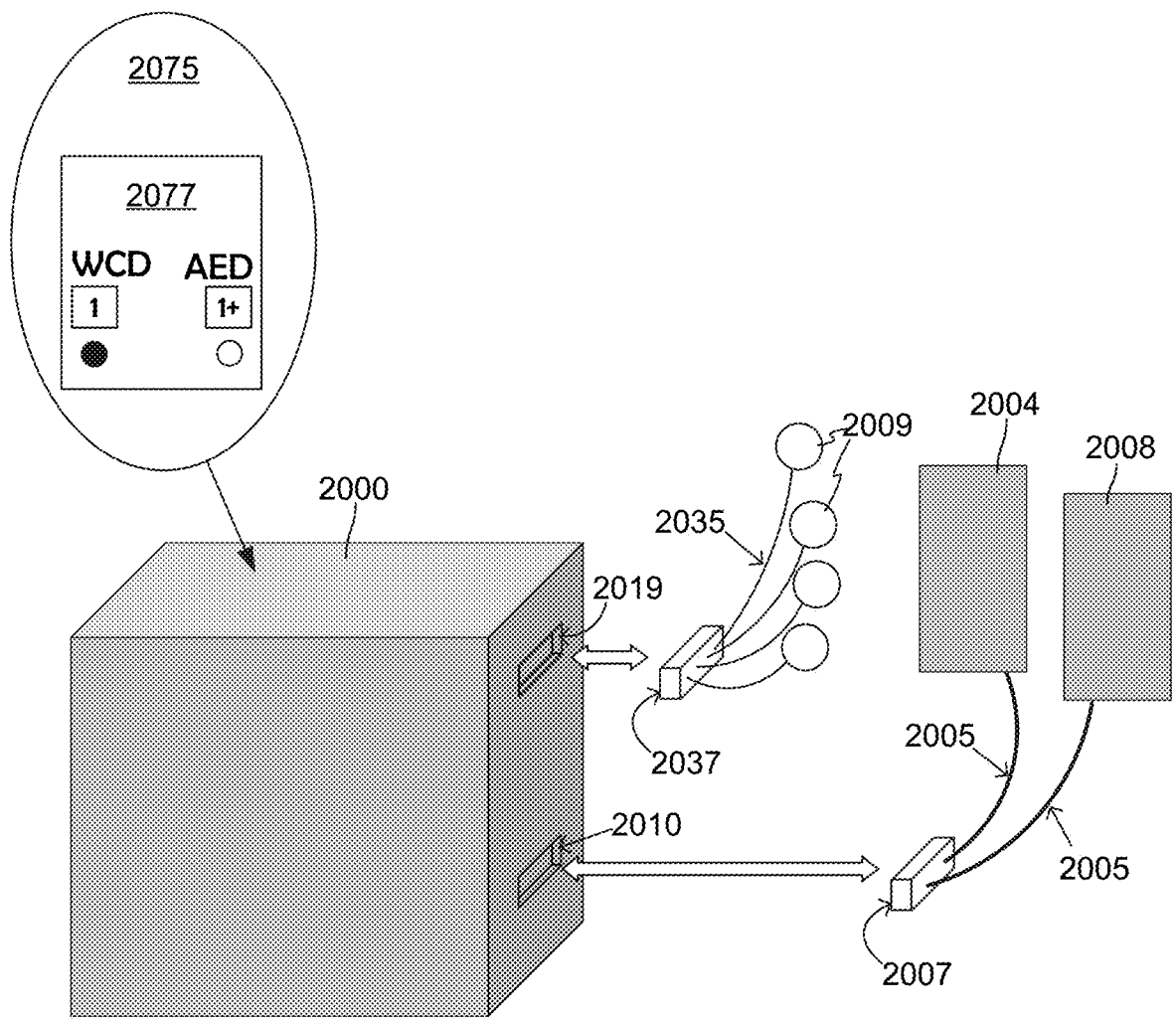
FIG. 20 is a diagram of sample components of a WCD system according to embodiments where the defibrillator collects ECG data from electrodes other than the defibrillation electrodes.

FIG. 20 is a diagram of a defibrillator 2000. According to a comment 2075, an indicator 2077 indicates that defibrillator 2000 or its processor is in a WCD mode, instead of in an AED mode. Defibrillator 2000 has a defibrillation socket 2010 that operates as a defibrillation port, and an ECG socket 2019 that operates as a sensor port.

A defibrillation electrode set includes electrode pads 2004, 2008, wire leads 2005 and a plug 2007. Plug 2007 can be configured to be plugged into and out of defibrillation socket 2010 as shown by an arrow. This defibrillation electrode set can be part of a WCD system used with defibrillator 2000 in a WCD mode, or AED electrodes that are used with defibrillator 2000 in an AED mode.

An ECG electrode set includes electrode pads 2009, wire leads 2035 and a plug 2037. Plug 2037 can be configured to be plugged into and out of ECG socket 2019 as shown by an arrow. Electrode pads 2009 are types of transducers that can help sense an ECG signal, e.g. a 12-lead signal, or a signal from a different number of leads, especially if they make good electrical contact with the body of the patient and in particular with the skin of the patient. When electrode pads 2009 are part of a WCD system, they can be coupled to the inside of the support structure, for example as seen for electrodes 609, 709 in FIGS. 6, 7. Alternately, electrode pads 2009 can be part of an AED system, supplementing AED defibrillation electrodes.

In the embodiment of FIG. 20, therefore, the ECG signal of patient 82 is collected from the ECG electrode set. In such embodiments, the sensor may further include an electrode additional to what is being described, which performs such ECG measurements. The additional electrode can be complementary to the first electrode, an ECG-only electrode, etc.

In the embodiment of FIG. 20, the two electrode sets have distinct plugs 2007, 2037 that can be plugged into distinct sockets 2010, 2019. This is shown to better describe the different functions, also for the two diagrams that follow. It is not necessary, however, for plugs 2007, 2037 to be distinct. Indeed, in some embodiments there is a single plug for both the defibrillation electrodes and, accordingly a single socket.

Two types of embodiments are now described for the internal workings of defibrillator 2000, for implementing AED modes more easily. First, in some embodiments of FIG. 20, the ECG signal is collected only via ECG socket 2019, but not also via defibrillation socket 2010. An example is now described.

Figure 21:
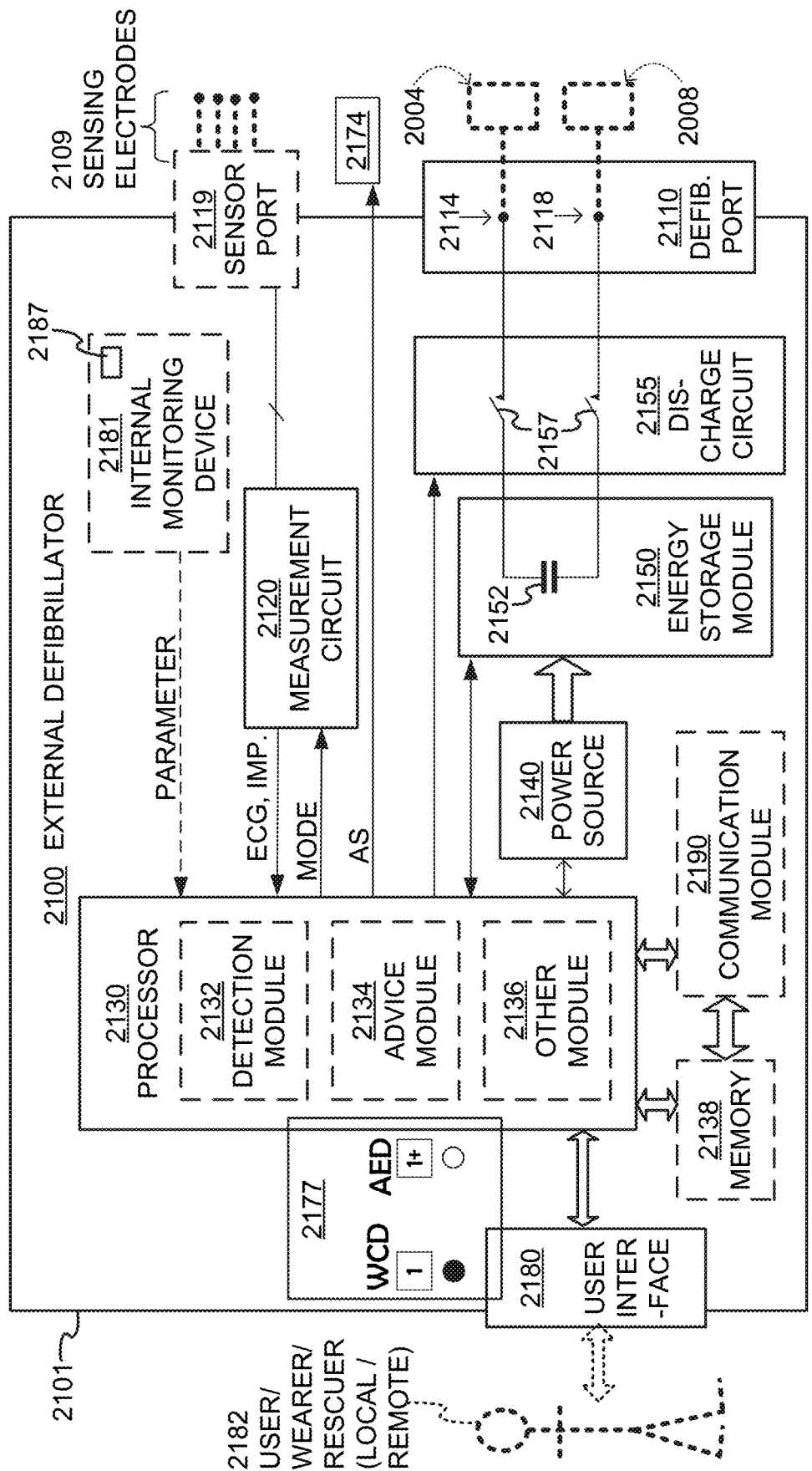
FIG. 21 is a diagram showing sample components of an external defibrillator, which is made according to embodiments that use separate electrodes for sensing the patient's ECG and for defibrillating the patient.

FIG. 21 is a diagram showing components of an external defibrillator 2100, made according to embodiments. These components can be, for example, included in external defibrillator 2000 of FIG. 20. User 2182 can be patient 82, or as described for user or rescuer 1982.

Much of what was described for FIG. 19 applies also for FIG. 21. In fact, components shown in FIG. 21 can be similar to similarly numbered components of FIG. 19, either identical or needing appropriate adjustments for the modes to be supported. In particular, a housing or casing 2101, a user interface 2180, an internal monitoring device 2181, a motion detector 2187, a processor 2130, a detection module 2132, an advice module 2134, another module 2136, an indicator 2177, a memory 2138, a power source 2140, an energy storage module 2150, a capacitor 2152, a discharge circuit 2155, switches 2157, a fluid deploying mechanism 2174 and a communication module 2190, can be as the previously described, with suitable adjustments, housing or casing 1901, user interface 1980, internal monitoring device 1981, motion detector 1987, processor 1930, detection module 1932, advice module 1934, other module 1936, indicator 1977, memory 1938, power source 1940, energy storage module 1950, capacitor 1952, discharge circuit 1955, switches 1957 and communication module 1990, respectively.

Defibrillator 2100 includes a defibrillation port 2110, which can be a socket in housing 2101, and also defibrillation socket 2010 of FIG. 20. Defibrillation port 2110 includes electrical nodes 2114, 2118. Leads of defibrillation electrodes 2004, 2008, can be plugged into defibrillation port 2110, so as to make electrical contact with nodes 2114, 2118, respectively. It is also possible that defibrillation electrodes 2004, 2008 are connected continuously to defibrillation port 2110, instead.

Defibrillator 2100 also has a sensor port 2119 in housing 2101, which is also sometimes known as an ECG port, and can be ECG socket 2019. Sensor port 2119 can be adapted for plugging in sensing electrodes 2109, which can also be the ECG electrodes of plug 2037. It is also possible that sensing electrodes 2109 can be connected continuously to sensor port 2119.

Defibrillator 2100 also includes a measurement circuit 2120, as one or more of its sensors or transducers. Measurement circuit 2120 senses one or more electrical physiological signals of the patient from sensor port 2119. The manner of sensing may be helped by a MODE signal from processor 2130, which indicates the prevalent mode. In these cases, the input reflects an ECG measurement. The patient parameter can be an ECG signal, and the patient input can include values for the ECG signal. In such embodiments, the sensor may include an electrode additional to what is being described, which performs such ECG measurements. In addition, the patient parameter can be an impedance, which can be sensed between the connections of sensor port 2119 considered pairwise. Sensing the impedance can be useful for detecting, among other things, whether sensing electrodes 2109 are not making good electrical contact with the patient's body. These patient physiological signals may be sensed when available. Measurement circuit 2120 can then render or generate information about them as inputs, data, other signals, etc. More strictly speaking, the information rendered by measurement circuit 2120 is output from it, but this information can be called an input because it is received as an input by a subsequent device or functionality.

Second, in other embodiments of FIG. 20, the ECG signal is collected via ECG socket 2019 in the WCD mode, and also via defibrillation socket 2010 in an AED mode. An example is now described.

Figure 22:
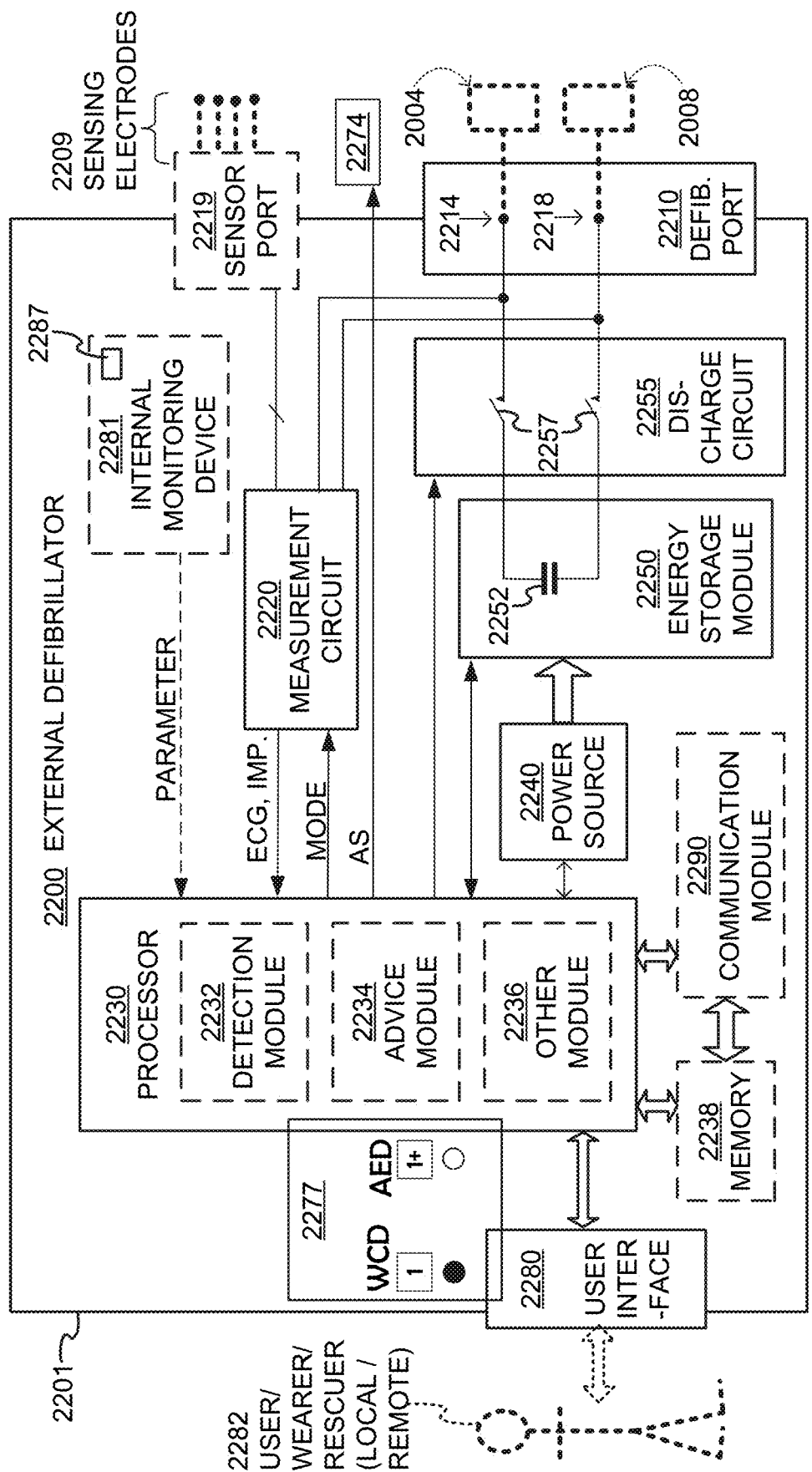
FIG. 22 is a diagram showing sample components of an external defibrillator, which is made according to an embodiment that uses an ECG electrode set and also a defibrillation electrode set for sensing the patient's ECG.

FIG. 22 is a diagram showing components of an external defibrillator 2200, made according to embodiments. These components can be, for example, included in external defibrillator 2000 of FIG. 20. User 2282 can be patient 82, or as described for user or rescuer 1982.

Much of what was described for FIG. 19 applies also for FIG. 22. In fact, components shown in FIG. 22 can be similar to similarly numbered components of FIG. 19, either identical or needing appropriate adjustments for the modes to be supported. In particular, a housing or casing 2201, a user interface 2280, an internal monitoring device 2281, a motion detector 2287, a processor 2230, a detection module 2232, an advice module 2234, another module 2236, an indicator 2277, a memory 2238, a power source 2240, an energy storage module 2250, a capacitor 2252, a discharge circuit 2255, switches 2257, a fluid deploying mechanism 2274 and a communication module 2290, can be as the previously described, with suitable adjustments, housing or casing 1901, user interface 1980, internal monitoring device 1981, motion detector 1987, processor 1930, detection module 1932, advice module 1934, other module 1936, indicator 1977, memory 1938, power source 1940, energy storage module 1950, capacitor 1952, discharge circuit 1955, switches 1957 and communication module 1990, respectively.

Defibrillator 2200 includes a defibrillation port 2210, which can be a socket in housing 2201, and also defibrillation socket 2010 of FIG. 20. Defibrillation port 2210 includes electrical nodes 2214, 2218. Leads of defibrillation electrodes 2004, 2008, can be plugged into defibrillation port 2210, so as to make electrical contact with nodes 2214, 2218, respectively. It is also possible that defibrillation electrodes 2004, 2008 are connected continuously to defibrillation port 2210, instead.

Defibrillator 2200 also has a sensor port 2219 in housing 2201, which is also sometimes known as an ECG port, and can be ECG socket 2019. Sensor port 2219 can be adapted for plugging in sensing electrodes 2209, which can also be the ECG electrodes of plug 2037. It is also possible that sensing electrodes 2209 can be connected continuously to sensor port 2219.

Defibrillator 2200 also includes a measurement circuit 2220, as one or more of its sensors or transducers. Measurement circuit 2220 senses one or more electrical physiological signals of the patient from sensor port 2219, for example in WCD mode, and/or through nodes 2214, 2218, for example in an AED mode, perhaps as an additional channel. In some embodiments, processor 2230 may give preferential treatment to the best available channel, which can be one received via electrodes that use pads with adhesive material, namely the AED electrodes at nodes 2214, 2218. Or, in an AED mode, that channel is the only one analyzed. The manner of sensing may be helped by a MODE signal from processor 2230, which indicates the prevalent mode. Or, measurement circuit 2220 may have a multi-lead ECG preamplifier connected to sensor port 2219, and a two-wire ECG preamplifier connected to defibrillation port 2210. The digitized signals could both be received by processor 2230. In the WCD mode processor 2230 may analyze the ECG signals from sensor port 2219, while ignoring the ECG signal from defibrillation port 2210. Conversely, in an AED mode processor 2230 may analyze the ECG signal from defibrillation port 2210, while ignoring the ECG signals from sensor port 2219. In these cases, the input reflects an ECG measurement. The patient parameter can be an ECG, which can be sensed as a voltage difference, and the patient input can include values for the ECG signal. As such, in an AED mode, some electrodes are used for both sensing the ECG and the defibrillation function. Of course, measurement circuit 2220 can have isolation to prevent the defibrillation discharge from harming it. In addition, the patient parameter can be an impedance, which can be sensed between electrodes 2004, 2008 and/or between the connections of sensor port 2219 considered pairwise. Sensing the impedance can be useful for detecting, among other things, whether these electrodes 2004, 2008 and/or sensing electrodes 2209 are not making good electrical contact with the patient's body. These patient physiological signals may be sensed when available. Measurement circuit 2220 can then render or generate information about them as inputs, data, other signals, etc. More strictly speaking, the information rendered by measurement circuit 2220 is output from it, but this information can be called an input because it is received as an input by a subsequent device or functionality.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for"

or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system for an ambulatory patient who is overseen by an attendant other than the ambulatory patient, the WCD system comprising:
a housing;
an energy storage module within the housing, the energy storage module configured to store an electrical charge;
a support structure configured to be worn by the patient;
a first electrode configured to be coupled to the housing, and configured to be coupled to the support structure for a WCD mode in which the patient is wearing the support structure so that the first electrode is maintained on a body of the patient when the support structure is worn by the patient, the first electrode further configured to be uncoupled from the support structure and to be attached to the body of the patient and coupled to the housing for an AED mode in which the patient is not wearing a portion of the support structure;
a sensor configured to sense a parameter of the patient and to render a patient input responsive to the sensed parameter;
a user interface that includes a shock input device configured to receive a shock input entered by the attendant; and
a processor configured to:
enter the WCD mode wherein in the WCD mode the processor is configured to cause a shock to be delivered responsive to a first shock criterion being met and to enter the AED mode distinct from the WCD mode wherein in the AED mode the processor is configured to cause a shock to be delivered responsive to the shock input entered by the attendant, wherein the processor enters the WCD mode or the AED mode responsive to an input received at the user interface or a default mode is entered after a preset time duration,
determine, from the patient input, when the first shock criterion is met,
cause, responsive to the first shock criterion being met, at least some of the stored electrical charge to be discharged via the first electrode through the patient so as to deliver a first shock to the patient when the support structure is worn by the patient, and
cause, responsive to the shock input being received, at least some of the stored electrical charge to be discharged via the first electrode through the patient to deliver a second shock to the patient, the second shock distinct from the first shock.

2. The WCD system of claim 1, in which
when the second shock is delivered, the patient is not wearing at least a portion of the support structure.

3. The WCD system of claim 1, in which
when the second shock is delivered, the patient is not wearing any portion of the support structure and the first electrode is uncoupled from the support structure, coupled with the housing, and attached to the body of patient for the AED mode.

4. The WCD system of claim 1, in which
the second shock is delivered when the first electrode is uncoupled from the support structure.

5. The WCD system of claim 1, in which
the second shock has energy higher than 50 joules.

6. The WCD system of claim 1, in which
the second shock has energy of at most 20 joules.

7. The WCD system of claim 1, in which
the shock input device of the user interface is located on the housing.

8. The WCD system of claim 1, in which
the processor is further configured to determine, from the patient input, when a second shock criterion is met, and
the user interface further includes an output device that is configured to emit a first human-perceptible indication responsive to the second shock criterion not being met.

9. The WCD system of claim 8, in which
the output device of the user interface is located on the housing.

10. The WCD system of claim 8, in which
the second shock criterion is the same as the first shock criterion.

11. The WCD system of claim 1, in which
the processor is further configured to determine, from the patient input, when a second shock criterion is met, and
the user interface further includes an output device that is configured to emit, responsive to the second shock criterion being met, a second human-perceptible indication.

12. The WCD system of claim 11, in which
the output device of the user interface is located on the housing.

13. The WCD system of claim 11, in which
the second shock criterion is the same as the first shock criterion.

14. The WCD system of claim 11, in which
when in the AED mode, the processor is configured to cause the second human-perceptible indication to be emitted, and
when in the WCD mode, the processor is configured to not cause the second human-perceptible indication to be emitted, even if the second shock criterion is met.

15. The WCD system of claim 14, in which
the second shock criterion is the same as the first shock criterion.

16. The WCD system of claim 14, in which
the processor is further configured to transition from being in one of the AED mode and the WCD mode to being in the other one of the AED mode and the WCD mode responsive to a transition condition being met.

17. The WCD system of claim 16, in which
the user interface further includes a mode selection input device that is configured to receive a mode selection input entered by the attendant, and
the transition condition is that the mode selection input is received by the mode selection input device.

18. The WCD system of claim 16, in which
the transition condition is that a preset time duration has passed during which the processor has been in the one of the AED mode and the WCD mode.

19. The WCD system of claim 16, in which
the processor is further configured to detect a certain electrical connection of the first electrode, and
the transition condition is that the certain electrical connection being detected.

20. The WCD system of claim 19, in which
the electrical connection is sensed by the presence of a signal on the first electrode.

21. A non-transitory computer-readable storage medium storing one or more programs which, when executed by at least one processor of a wearable cardioverter defibrillator (WCD) system for an ambulatory patient who is overseen by an attendant other than the ambulatory patient, the WCD system including a housing, an energy storage module within the housing, the energy storage module configured to store an electrical charge, a support structure configured to be worn by the patient, a first electrode configured to be coupled to the housing, and configured to be coupled to the support structure so that the first electrode is maintained on a body of the patient when the support structure is worn by the patient, the first electrode further configured to be uncoupled from the support structure, a sensor configured to sense a parameter of the patient and render a patient input responsive to the sensed parameter of the patient, and a user interface that includes a shock input device, these one or more programs result in operations comprising:

determining, from the patient input, when a first shock criterion is met;
 causing, responsive to the first shock criterion being met, at least some of the stored electrical charge to be discharged via the first electrode through the patient so as to deliver a first shock to the patient when the support structure is worn by the patient;
 receiving, by the shock input device, a shock input entered by the attendant; and causing, responsive to the shock input being received, at least some of the stored electrical charge to be discharged via the first electrode through the patient to deliver a second shock to the patient;
 entering, via the processor, a WCD mode in which the patient is wearing the support structure, wherein in the WCD mode the processor is configured to cause a shock to be delivered responsive to the first shock criterion being met; and
 entering, via the processor, an AED mode distinct from the WCD mode in which the patient is not wearing a portion of the support structure, wherein the first electrode is configured to attach to the patient when the first electrode is uncoupled from the support structure and coupled with the housing for the AED mode, wherein in the AED mode the processor is configured to cause a shock to be delivered responsive to the shock input entered by the attendant;
 wherein the WCD mode or the AED mode is entered responsive to an input received at the user interface or a default mode is entered after a preset time duration.

22. A method for a wearable cardioverter defibrillator (WCD) system for an ambulatory patient who is overseen by an attendant other than the ambulatory patient, the WCD system including a housing, an energy storage module within the housing, the energy storage module configured to store an electrical charge, a support structure configured to be worn by the patient, a first electrode configured to be coupled to the housing, and configured to be coupled to the support structure so that the first electrode is maintained on a body of the patient when the support structure is worn by the patient, the first electrode further configured to be uncoupled from the support structure, a sensor configured to sense a parameter of the patient, a user interface that includes a shock input device, and a processor, the method comprising:

rendering, by the sensor, a patient input responsive to the sensed parameter of the patient;
 determining, from the patient input, when a first shock criterion is met;
 causing, responsive to the first shock criterion being met, at least some of the stored electrical charge to be discharged via the first electrode through the patient so as to deliver a first shock to the patient when the support structure is worn by the patient;
 receiving, by the shock input device, a shock input entered by the attendant; and causing, responsive to the shock input being received, at least some of the stored electrical charge to be discharged via the first electrode through the patient to deliver a second shock to the patient;
 entering, via the processor, a WCD mode in which the patient is wearing the support structure, wherein in the WCD mode the processor is configured to cause a shock to be delivered responsive to the first shock criterion being met; and
 entering, via the processor, an AED mode distinct from the WCD mode in which the patient is not wearing a portion of the support structure, wherein the first electrode is configured to attach to the patient when the first electrode is uncoupled from the support structure and coupled with the housing for the AED mode, wherein in the AED mode the processor is configured to cause a shock to be delivered responsive to the shock input entered by the attendant;
 wherein the WCD mode or the AED mode is entered responsive to an input received at the user interface or a default mode is entered after a preset time duration.

\* \* \* \* \*